United States Patent [19]
Adams et al.

[11] Patent Number: 5,145,858
[45] Date of Patent: Sep. 8, 1992

[54] PYRROLO [1,2-a] IMIDAZOLE AND IMIDAZO [1,2-a] PYRIDINE DERIVATIVES AND THEIR USE AS 5-LIPOXYGENASE PATHWAY INHIBITORS

[75] Inventors: Jerry L. Adams, Wayne, Pa.; Paul E. Bender, Cherry Hill, N.J.; John G. Gleason, Downingtown, Pa.; Nabil Hanna, Berwyn, Pa.; John F. Newton, Jr., West Chester, Pa.; Carl D. Perchonock, Bethesda, Md.

[73] Assignee: SmithKline Beecham Corp., Philadelphia, Pa.

[21] Appl. No.: 815,543

[22] Filed: Dec. 26, 1991

Related U.S. Application Data

[60] Continuation of Ser. No. 624,005, Dec. 7, 1990, which is a division of Ser. No. 255,816, Oct. 11, 1988, Pat. No. 5,002,941, which is a continuation of Ser. No. 92,258, Sep. 2, 1987, abandoned, which is a continuation-in-part of Ser. No. 856,928, Apr. 28, 1986, Pat. No. 4,719,218, which is a continuation-in-part of Ser. No. 808,407, Dec. 12, 1985, abandoned.

[51] Int. Cl.$^5$ ................... A61K 31/40; C07D 471/04; C07D 413/04
[52] U.S. Cl. ..................... 514/318; 514/300; 514/316; 514/338; 514/824; 546/121; 546/187; 546/193; 546/194; 546/271
[58] Field of Search ............... 546/121, 187, 193, 194, 546/271; 514/300, 316, 318, 338, 824

[56] References Cited

U.S. PATENT DOCUMENTS

| | | | |
|---|---|---|---|
| 3,823,297 | 7/1974 | Fox et al. | 548/324 |
| 4,064,260 | 12/1977 | Cherkofsky et al. | 548/324 |
| 4,110,460 | 8/1978 | Baetz et al. | 548/324 |
| 4,153,706 | 5/1979 | Bender et al. | 548/324 |
| 4,175,127 | 11/1979 | Bender et al. | 548/324 |
| 4,186,205 | 1/1980 | Bender et al. | 548/324 |
| 4,263,311 | 4/1981 | Bender et al. | 548/324 |
| 4,507,481 | 3/1985 | Davidson et al. | 548/324 |
| 4,621,110 | 11/1986 | DiBattista | 548/324 |

FOREIGN PATENT DOCUMENTS

| | | | |
|---|---|---|---|
| 154494 | 9/1985 | European Pat. Off. | 548/324 |
| 0231622 | 8/1987 | European Pat. Off. | |
| 1180202 | 2/1970 | United Kingdom | 548/324 |
| 2039882 | 8/1980 | United Kingdom | 548/324 |

OTHER PUBLICATIONS

Mohrle, H. et al., *Arch. Pharm.* 316, pp. 47–55 (1983).
Claxton, G. et al., *J. Med. Chem.*, 17, 3, 364–367 (1974).
*Chem. Abs.* 11994 q, vol. 82, p. 507 (1975).
Lantos et al., *J. Med. Chem*, 27, 72–75 (1984).
Lantos et al. U.S. Ser. No. 856,246 filed Apr. 28, 1986.
Bender et al., *J. Med. Chem.*, 28, 1169–1177 (1985).
Bender et al., U.S. Ser. No. 106,199 filed Oct. 7, 1987.
Kano, S. *J. Pharm. Soc.* Japan, 92, 1, 55–58 (1972).
Andreani, A. et al., *Arch. Pharm.* (Weinheim), 315, 451–456 (1982).
Schoberl, A. et al., *Liebigs Ann. Chem.* 742, 85–97 (1970).
Lee, M. H., et al. *Biochemical Pharmacology*, 24, 1175–1178 (1975).
Andreani, A. et al. *Eur. J. Med. Chem.* 19, 3 219–222 (1984).

*Primary Examiner*—Johann Richter
*Attorney, Agent, or Firm*—Dara L. Dinner; Stuart R. Suter; Edward T. Lentz

[57] ABSTRACT

Compounds comprising pyridyl and phenyl substituted pyrrolo[1,2-a]imidazole derivatives and pyridyl and phenyl substituted imidazo[1,2-a]pyridine derivatives, pharmaceutical compositions containing said compounds, and their use as 5-lipoxygenase pathway inhibitors.

15 Claims, No Drawings

PYRROLO [1,2-a] IMIDAZOLE AND IMIDAZO [1,2-a] PYRIDINE DERIVATIVES AND THEIR USE AS 5-LIPOXYGENASE PATHWAY INHIBITORS

CROSS REFERENCE TO RELATED APPLICATIONS

This is a continuation of application Ser. No. 07/624,005, filed Dec. 7, 1990, which is a divisional of application Ser. No. 07/255,816, filed Oct. 11, 1988, now U.S. Pat. No. 5,002,941, which is a continuation of application Ser. No. 07/092,258, filed Sep. 2, 1987, now abandoned, which is a continuation-in-part of application Ser. No. 856,928, filed Apr. 28, 1986, now U.S. Pat. No. 4,719,218 which is a continuation-in-part of application Ser. No. 808,407, filed Dec. 12, 1985, which is abandoned.

BACKGROUND OF THE INVENTION

This invention relates to novel compounds, pharmaceutical compositions and methods of inhibiting the 5-lipoxygenase pathway of arachidonic acid metabolism in an animal in need thereof which comprises administering to such animal an effective, 5-lipoxygenase pathway inhibiting amount of a pyridyl and phenyl substituted pyrrolo[1,2-a]imidazole, or pyridyl and phenyl substituted imidazo[1,2-a]pyridine, or a pharmaceutically acceptable salt thereof.

Davidson et al., U.S. Pat. No. 4,507,481, issued Mar. 26, 1985, disclose compounds of the formula:

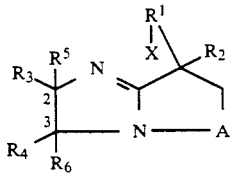

wherein:
X is O or S(O)n;
n is O, 1 or 2;
$R^1$ is H, lower alkyl, phenyl, benzyl or benzyl substituted with lower alkylamino, lower alkylamino, nitro, halo, hydroxy or lower alkoxy-;
$R_2$ is H or $XR^1$;
A is $CH_2$ or $CH_2CH_3$;
$R_3$ and $R_4$ are independently selected from A, lower alkyl, aryl, aryl substituted with lower alkyl, amino, lower alkylamino, nitro, lower alkoxy, hydroxy or halogen; provided that at least one of $R_3$ and $R_4$ is aryl or substituted aryl; and
$R_5$ and $R_6$ are each H or join to form a double bond at the 2,3-position.

Davidson et al. also disclose that such compounds are immunostimulants or immunosuppresants based on (a) their inhibiting or stimulating activity in a chemotaxis assay which measures the ability of a drug substance to influence the movement of murine macrophages responding to complement; (b) their immunosuppressing or activating activity in the Kennedy plaque assay in which an animal's humoral immune system is depressed artificially with 6-mercaptopurine. Neither the chemotaxis assay nor the Kennedy plaque assay is of any known utility for detecting or suggesting compounds which are inhibitors of the 5-lipoxygenase pathway. Davidson et al. also disclose that such compounds have antiinflammatory activity as determined by the carrageenan-induced paw edema assay in rats. As stated above, such assay has no known utility in detecting or suggesting compounds which are inhibitors of the 5-lipoxygenase pathway. Davidson et al. also disclose that such compounds have antiviral activity in mice with hepatitis; but such activity is of no known utility in detecting or suggesting compounds which are inhibitors of the 5-lipoxygenase pathway.

SUMMARY OF THE INVENTION

This invention relates to a compound of the formula (I)

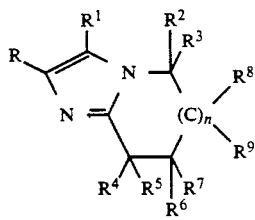

FORMULA (I)

wherein
1) One of R or $R^1$ must be alkyl substituted pyridyl and the other is selected from:
 (a) monosubstituted phenyl wherein said substituent is selected from H, halo, hydroxy $C_{1-3}$ alkoxy, $C_{1-3}$ alkylthio, $C_{1-4}$ alkyl, $C_{1-3}$ alkylsulfinyl, $C_{1-3}$ alkylsulfonyl, $C_{1-3}$ alkylamino, $C_{1-3}$ dialkylamino, $CF_3$, N-($C_{1-3}$ alkyl)-N-($C_{1-3}$alkanamido), N-pyrrolidino, N-piperidino, prop-2-ene-1-oxy or 2,2,2-trihaloethoxy;
 (b) disubstituted phenyl wherein said substituents are the same and are selected from halo, $C_{1-3}$ alkoxy, $C_{1-3}$ alkylamino, $C_{1-3}$ dialkylamino, N-pyrrolidino, N-piperidino, 2,2,2-trihaloethoxy, prop-2-ene-1-oxy, or hydroxy, or the disubstituents together form a methylene dioxy group;
 (c) disubstituted phenyl wherein said substituents are not the same and are independently selected from halo, $C_{1-3}$ alkylamino, nitro, N-($C_{1-3}$alkyl)-N-($C_{1-3}$ alkanamido, $C_{1-3}$ dialkylamino, amino, N-pyrrolidino or N-piperidino;
 (d) disubstituted phenyl wherein one of said substituents must be $C_{1-3}$ alkoxy, hydroxy, 2,2,2-trihaloethoxy or prop-2-ene-1-oxy and the other substituent is independently selected from halo, $C_{1-3}$ alkylamino, N-($C_{1-3}$alkyl)-N-$C_{1-3}$alkanamido), $C_{1-3}$dialkylamino, amino, N-pyrrolidino or N-piperidino; or
 (e) disubstituted phenyl wherein one substituent is selected from $C_{1-3}$ alkylthio, $C_{1-3}$ alkylsulfinyl, and $C_{1-3}$ alkylsulfonyl and the other is selected from $C_{2-3}$ alkoxy, nitro, halo, amino, $C_{1-3}$ alkylamino, or $C_{1-3}$ dialkylamino; or
2) One of R or $R^1$ is 2-pyridyl or 3-pyridyl and the other is selected from:
 (a) monosubstituted phenyl wherein said substituent is selected from $C_{1-3}$ alkylthio, $C_{1-3}$ alkylsulfinyl, $C_{1-3}$ alkylsulfonyl, $C_{1-3}$ alkoxy or hydroxy; or
 (b) disubstituted phenyl wherein one substituent is selected from $C_{1-3}$ alkylthio, $C_{1-3}$ alkylsulfinyl, or $C_{1-3}$ alkylsulfonyl and the other is selected from $C_{1-3}$ alkoxy, nitro, halo, amino, $C_{1-3}$ alkylamino, or $C_{1-3}$ dialkylamino; or

3

R is 4-pyridyl and $R^1$ is selected from:
  (a) monosubstituted phenyl wherein said substituent is selected from $C_{1-3}$ alkylthio, $C_{1-3}$ alkylsulfinyl, $C_{1-3}$ alkylsulfonyl or hydroxy; or
  (b) disubstituted phenyl wherein one substituent is selected from $C_{1-3}$ alkylthio, $C_{1-3}$ alkylsulfinyl, or $C_{1-3}$ alkylsulfonyl and the other is selected from $C_{2-3}$ alkoxy, nitro, halo, amino, $C_{1-3}$ alkylamino, or $C_{1-3}$ dialkylamino; or $R^1$ is 4-pyridyl and R selected from:
  (a) monosubstituted phenyl wherein said substituent is selected from $C_{1-3}$ alkylthio, $C_{1-3}$ alkylsulfinyl, $C_{1-3}$ alkylsulfonyl, hydroxy or $C_{2-3}$ alkoxy, or branched or unbranched $C_{2-5}$ alkenylthio or $C_{2-5}$ alkenylsulfinyl; or
  (b) disubstituted phenyl wherein one substituent is selected from $C_{1-3}$ alkylthio, $C_{1-3}$ alkylsulfinyl, or $C_{1-3}$ alkylsulfonyl and the other is selected from $C_{2-3}$ alkoxy, nitro, halo, amino, $C_{1-3}$ alkylamino, or $C_{1-3}$ dialkylamino, or branched or unbranched $C_{2-5}$ alkenylthio or $C_{2-5}$ alkenylsulfinyl; or One of $R^1$ or R is pyridyl or alkyl substituted pyridyl and the other is
  (a) monosubstituted phenyl wherein said substituent is from alkenylthio, alkenylsulfinyl, thiol [HS-], acylthio [AC(O)S-], dithioacyl [AC(S)S-], thiocarbamyl [AA$^1$NC(O)S-], dithiocarbamyl [AA$^1$NC(S)S-], alkylcarbonylalkylthio [AC(O)CH$_2$S-], carbalkoxyalkylthio [BOC(O)CH$_2$S-], alkoxycarbonylthio [BOC(O)S-], alkoxythionothio[BOC(S)S-], phenylthio, alkoxyalkylthio[BOCH$_2$S-], alkoxyalkylsulfinyl[BOCH$_2$S(O)], alkylthioalkylthio [BSCH$_2$S-], disulfide [BSS-], or acyloxyalkylthio [AC(O)OCH$_2$S ] wherein the CH$_2$ is optionally substituted with $C_{1-4}$alkyl, and A and A$^1$ are hydrogen, $C_{1-9}$alkyl or phenyl and B is $C_{1-9}$alkyl or phenyl;
  b) disubstituted phenyl wherein the substituents are the same and are selected from $C_{1-3}$ alkylthio, $C_{1-3}$ alkylsulfinyl, $C_{1-3}$ alkylsulfonyl, alkenylthio, alkenylsulfinyl, thiol [HS-], acylthio [AC(O)S-], dithioacyl [AC(S)S-], thiocarbamyl [AA$^1$NC(O)S ], dithiocarbamyl [AA$^1$NC(S)S ], alkylcarbonylalkylthio [AC(O)CH$_2$S ], carbalkoxyalkylthio [BOC(O)CH$_2$S ], alkoxycarbonylthio [BOC(O)S-], alkoxythionothio[BOC(S)S-], phenylthio, alkoxyalkylthio[BOCH$_2$S ], alkoxyalkylsulfinyl[BOCH$_2$S(O)], alkylthioalkylthio [BSCH$_2$S-], disulfide [BSS-], or acyloxyalkylthio [AC(O)OCH$_2$S-]wherein the CH$_2$ is optionally substituted with $C_{1-4}$alkyl, and A and A$^1$ are hydrogen, $C_{1-9}$alkyl or phenyl, and B is $C_{1-9}$alkyl or phenyl; or
  (c) disubstituted phenyl wherein one substituent is selected from $C_{2-3}$ alkoxy, nitro, halo, amino, $C_{1-3}$ alkylamino, $C_{1-3}$ dialkylamino and the other is selected from alkenylthio, alkenylsulfinyl, thiol [HS ], acylthio [AC(O)S-], dithioacyl [AC(S)S-], thiocarbamyl [AA$^1$NC(O)S-], dithiocarbamyl [AA$^1$NC(S)S-], alkylcarbonylalkylthio [AC(O)CH$_2$S-], carbalkoxyalkylthio [BOC(O)CH$_2$S-], alkoxycarbonylthio [BOC(O)S-], alkoxythionothio[BOC(S)S-], phenylthio, alkoxyalkylthio[BOCH$_2$S-], alkoxyalkylsulfinyl[BOCH$_2$S(O)], alkylthioalkylthio [BSCH$_2$S-], disulfide [BSS-], or acyloxyalkylthio [AC(O)OCH$_2$S-] wherein the CH$_2$ is optionally substituted with $C_{1-4}$alkyl, and A and A$^1$ are

4 hydrogen, $C_{1-9}$alkyl or phenyl, and B is $C_{1-9}$alkyl or phenyl; or

One of $R^1$ or R is pyridyl or alkyl substituted pyridyl and the other is selected from monosubstituted phenyl wherein said substituent is

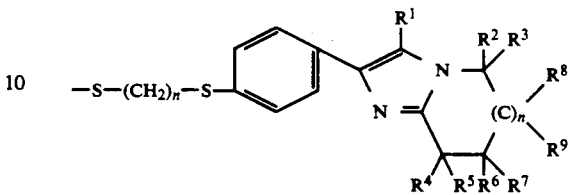

wherein
$R^1$ is pyridyl or alkyl substituted pyridyl and $R^2$, $R^3$, $R^4$, $R^5$, $R^6$, $R^7$, and $R^9$ are defined as in formula (I);
and $R^2$, $R^3$, $R^4$, $R^5$, $R^6$, $R^7$, $R^8$ and $R^9$ are H, or one or two of $R^2$, $R^3$, $R^3$, $R^4$, $R^5$, $R^6$, $R^7$, and $R^9$ are independently selected from H or $C_{1-2}$ alkyl; and n is 0 or 1;
or a pharmaceutically acceptable salt thereof.

The term N ($C_{1-2}$ alkyl)-N-($C_{1-3}$ alkanamido) is used herein at all occurrences to mean one of the following:

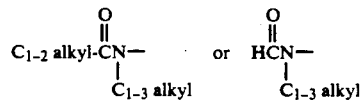

This invention also relates to a pharmaceutical composition comprising a pharmaceutically acceptable carrier or diluent and an effective, non toxic 5--lipoxygenase pathway inhibiting amount of a compound of the formula (I) as defined above, or a pharmaceutically acceptable salt thereof.

This invention also relates to a method of treating a 5-lipoxygenase pathway mediated disease in an animal in need thereof which comprises administering to such animal an effective, non toxic 5-lipoxygenase pathway inhibiting amount of a compound of Formula (I) as defined above, or a pharmaceutically acceptable salt thereof.

This invention also relates to intermediate compounds used in the preparation of a compound of Formula (I) having the following structural formula (J):

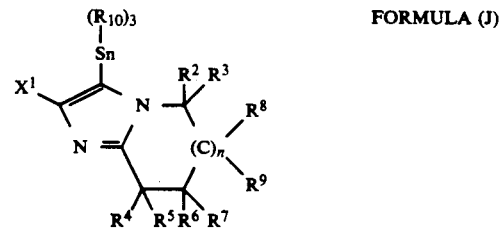

FORMULA (J)

wherein
n is 0 or 1;
$R^2$, $R^3$, $R^4$, $R^5$, $R^6$, $R^7$, $R^8$ and $R^9$ are H, or one or two of $R^2$, $R^3$, $R^4$, $R^5$, $R^6$, $R^7$, $R^8$ and $R^9$ are independently selected from H or $C_{1-2}$ alkyl;
$R_{10}$ is $C_{1-4}$ alkyl;
and $X^1$ is selected from
  (a) phenyl or monosubstituted phenyl wherein said substituent is selected from H, fluoro, chloro, $C_{1-3}$ alkoxy, $C_{1-4}$ alkyl, $C_{1-3}$ alkylthio, $C_{1-3}$ dialkylamino, $CF_3$, $C_{1-3}$ alkylamino, N-pyrrolidino, N-piperidino, prop-2-ene-1-oxy or 2,2,2-trihaloethoxy;

(b) disubstituted phenyl wherein said substituents are the same and are selected from fluoro, chloro, $C_{1-3}$ alkoxy, $C_{1-3}$ dialkylamino, N-pyrrolidino, N-piperidino, 2,2,2-trihaloethoxy, prop-2-ene-1-oxy, or the disubstituents together form a methylene dioxy group;

(c) disubstituted phenyl wherein said substituents are not the same and are independently selected from fluoro, chloro, $C_{1-3}$ alkylamino, $C_{1-3}$ dialkylamino, N-pyrrolidino, or N-piperidino;

(d) disubstituted phenyl wherein one of said substituents must be $C_{1-3}$ alkoxy, 2,2,2-trihaloethoxy or prop-2-ene-1-oxy and the other substituent is independently selected from fluoro, chloro, $C_{1-3}$ alkylamino, $C_{1-3}$ dialkylamino, N-pyrrolidino or N-piperidino; or (e) pyridyl or alkyl substituted pyridyl.

This invention also relates to intermediate compounds used in the preparation of a compound of Formula (I) having the following structural Formula (L):

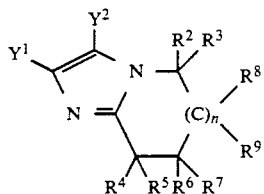

FORMULA (L)

wherein:
n is 0 or 1,
$R^2$, $R^3$, $R^4$, $R^5$, $R^6$, $R^7$, $R^8$, $R^9$ are all H, or one or two of $R^2$, $R^3$, $R^4$, $R^5$, $R^6$, $R^7$, and $R^9$, are independently selected from H or $C_{1-2}$ alkyl;
one of $Y^1$ or $Y^2$ is independently selected from 4-[1,2-dihydro-2-($C_{1-4}$-alkyl)pyridyl substituted with N-($C_{1-8}$ alkanoyl), N-($C_{1-8}$ alkoxycarbonyl), N-(benzoyl), N-(phenoxycarbonyl), N-(phenylacetyl), or N-(benzyloxycarbonyl);

and the other is selected from (a) monosubstituted phenyl wherein said substituent is selected from H, halo, $C_{1-3}$ alkoxy, $C_{1-3}$ alkylthio, $C_{1-4}$ alkyl, N-($C_{1-3}$ alkyl)-N-($C_{1-3}$ alkanamido), $C_{1-3}$ dialkylamino, $CF_3$, N-pyrrolidino, N-piperidino, prop-2-ene-1-oxy or 2,2,2-trihaloethoxy;

(b) disubstituted phenyl wherein said substituents are the same and are selected from halo, $C_{1-3}$ alkoxy, $C_{1-3}$ dialkylamino, $C_{1-3}$alkylthio, N-pyrrolidino, N-piperidino, 2,2,2-trihaloethoxy, or prop-2-ene-1-oxy, or the disubstituents together form a methylene dioxy group;

(c) disubstituted phenyl wherein said substituents are not the same and are independently selected from halo, N-($C_{1-3}$ alkyl)-N-($C_{1-3}$ alkanamido), $C_{1-3}$ dialkylamino, N-pyrrolidino, or N-piperidino; or (d) disubstituted phenyl wherein one of said substituents must be $C_{1-3}$ alkoxy, $C_{1-3}$ alkylthio, 2,2,2-trihaloethoxy or prop-2-ene-1-oxy and the other substituent is independently selected from halo, $C_{1-3}$ alkylamino, N-($C_{1-3}$ alkyl)-N-($C_{1-3}$ alkanamido), $C_{1-3}$dialkylamino, N-pyrrolidino, or N-piperidino;

or a salt thereof.

DETAILED DESCRIPTION OF THE INVENTION

This invention relates to compounds of Formula (I) as described above, pharmaceutical compositions comprising a pharmaceutically acceptable carrier or diluent and a compound of Formula (I), methods of treating 5-lipoxygenase pathway mediated diseases comprising administration of a compound of Formula (I) or a pharmaceutical composition containing a compound of Formula (I). This invention also relates to compounds of Formula (J) and (L) as described above.

All of the compounds of Formula (I) are useful in inhibiting the 5-lipoxygenase pathway of arachidonic acid metabolism in an animal in need thereof.

The compounds of Formula (I) can be prepared according to the following synthetic route:

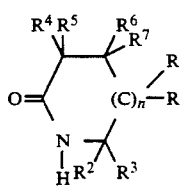 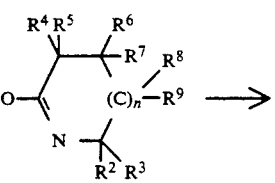

FORMULA (A)   FORMULA (B)

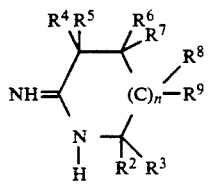 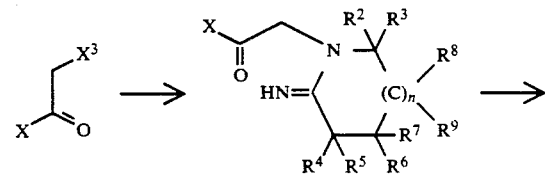

FORMULA (C)   FORMULA (D)   FORMULA (H)

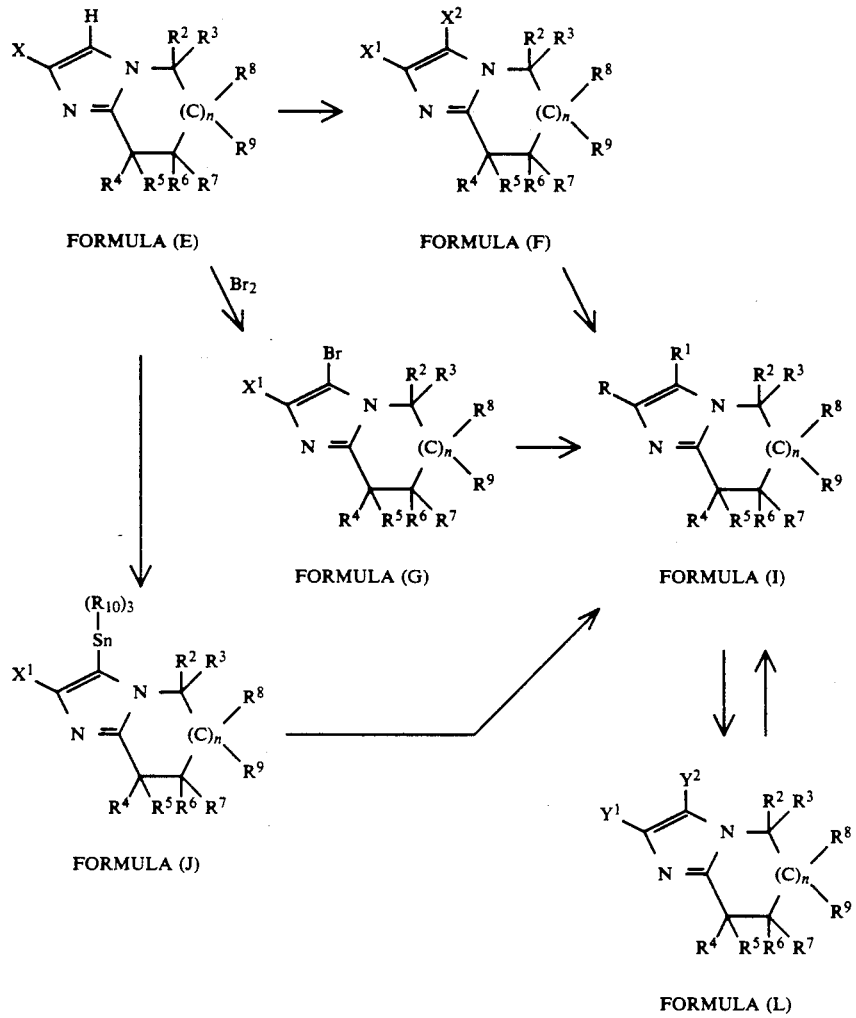

FORMULA (E)

FORMULA (F)

FORMULA (G)

FORMULA (I)

FORMULA (J)

FORMULA (L)

All the compounds of Formula (E), Formula (F), Formula (G), Formula (H), Formula (J) and Formula (L) are useful as intermediates in the preparation of compounds of Formula (I). All of the necessary compounds of Formula (A), Formula (B), Formula (C) and Formula (D) can be obtained from commercial sources or are preparable by conventional techniques such as those set out herein.

The compounds of Formula (E) have the following structure

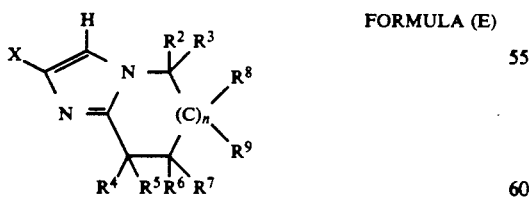

FORMULA (E)

wherein
n is 0 or 1;
$R^2$, $R^3$, $R^4$, $R^5$, $R^6$, $R^7$, $R^8$ and $R^9$ are H, or one or two of $R^2$, $R^3$, $R^4$, $R^5$, $R^6$, $R^7$, $R^8$ and $R^9$ are independently selected from H or $C_{1-2}$ alkyl;
X is selected from:
(a) pyridyl;

(b) monosubstituted phenyl, wherein said substituent is selected from halo, $C_{1-3}$ alkoxy, amino, hydroxy, $C_{1-3}$ alkylthio, $C_{1-4}$ alkyl, $C_{1-3}$ alkylamino, $C_{1-3}$ dialkylamino, $CF_3$, N-($C_{1-3}$ alkanamido), N-($C_{1-3}$ alkyl)-N-($C_{1-3}$ alkanamido), N-pyrrolidino, N-piperidino, prop-2-ene-1-oxy or 2,2,2-trihaloethoxy;

(c) disubstituted phenyl wherein said substituents are the same and are selected from halo, $C_{1-3}$ alkoxy, $C_{1-3}$ alkylthio, $C_{1-3}$ alkylamino, $C_{1-3}$ dialkylamino, amino, N-pyrrolidino, N-piperidino, 2,2,2-trihaloethoxy, prop-2-ene-1-oxy, hydroxy, or the disubstituents together form a methylene dioxy group;

(d) disubstituted phenyl wherein said substituents are not the same and are independently selected from halo, $C_{1-3}$ alkylamino, nitro, N-($C_{1-3}$ alkanamido), N-($C_{1-3}$ alkyl)-N-($C_{1-3}$ alkanamido), $C_{1-3}$ dialkylamino, amino, N-pyrrolidino, or N-piperidino; or (e) disubstituted phenyl wherein one of said substituents must be $C_{1-3}$ alkoxy, hydroxy, $C_{1-3}$ alkylthio, 2,2,2-trihaloethoxy or prop-2-ene-1-oxy and the other substituent is independently selected from halo, $C_{1-3}$ alkylamino, nitro, N-($C_{1-3}$ alkyl)-N-($C_{1-3}$ alkanamido), $C_{1-3}$ dialkylamino, amino, N-pyrrolidino, or N-piperidino;

provided that when n is 1, and $R^2$, $R^3$, $R^4$, $R^5$, $R^6$, $R^7$, $R^8$ and $R^9$ are H, X is other than 2,4-dimethoxyphenyl or 4-aminophenyl; or a salt thereof.

A further intermediate compound used in the preparation of a compound of Formula (I) is a compound of the formula:

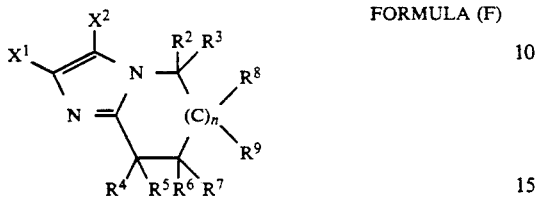

FORMULA (F)

wherein:

n is 0 or 1, $R^2$, $R^3$, $R^4$, $R^5$, $R^6$, $R^7$, $R^8$ and $R^9$ are all H, or one or two of $R^2$, $R^3$, $R^4$, $R^5$, $R^6$, $R^7$, $R^8$ and $R^9$, are independently selected from H or $C_{1-2}$ alkyl;

$X^2$ is 4-(1,4-dihydro)pyridyl substituted with N-($C_{1-8}$ alkanoyl), N-($C_{1-8}$ alkoxycarbonyl), N-(benzoyl), N-(phenoxycarbonyl), N-(phenylacetyl), or N-(benzyloxycarbonyl);

$X^1$ is selected from
  (a) monosubstituted phenyl wherein said substituent is selected from H, halo, $C_{1-3}$ alkoxy, hydroxy, $C_{1-3}$ alkylthio, $C_{1-4}$ alkyl, N-($C_{1-3}$ alkyl)-N-($C_{1-3}$ alkanamido), $C_{1-3}$ dialkylamino, $CF_3$, N-pyrrolidino, N-piperidino, prop-2-ene-1-oxy or 2,2,2-trihaloethoxy;
  (b) disubstituted phenyl wherein said substituents are the same and are selected from halo, $C_{1-3}$ alkoxy, $C_{1-3}$ dialkylamino, $C_{1-3}$ alkylthio, N-pyrrolidino, N-piperidino, 2,2,2-trihaloethoxy, or prop-2-ene-1-oxy, or the disubstituents together form a methylene dioxy group;
  (c) disubstituted phenyl wherein said substituents are not the same and are independently selected from halo, nitro, hydroxy, N-($C_{1-3}$ alkyl)-N-($C_{1-3}$ alkanamido), $C_{1-3}$ dialkylamino, N-pyrrolidino, or N-piperidino; or
  (d) disubstituted phenyl wherein one of said substituents must be $C_{1-3}$ alkoxy, hydroxy, $C_{1-3}$ alkylthio, 2,2,2-trihaloethoxy or prop-2-ene-1-oxy and the other substituent is independently selected from halo, $C_{1-3}$ alkylamino, nitro, N-($C_{1-3}$ alkyl)-N-($C_{1-3}$ alkanamido), $C_{1-3}$dialkylamino, amino, N-pyrrolidino, or N-piperidino; or a salt thereof.

A further intermediate compound used in the preparation of a compound of Formula (I) is a compound of the formula:

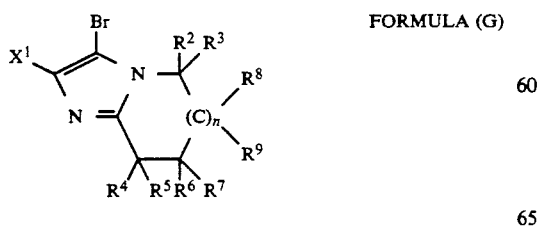

FORMULA (G)

wherein:
n is 0 or 1, $R^2$, $R^3$, $R^4$, $R^5$, $R^6$, $R^7$, $R^8$ and $R^9$ are all H, or one or two of $R^2$, $R^3$, $R^4$, $R^5$, $R^6$, $R^7$, $R^8$, and $R^9$ are independently selected from H or $C_{1-2}$ alkyl; and $X^1$ is selected from
  (a) monosubstituted phenyl wherein said substituent is selected from H, fluoro, chloro, $C_{1-3}$ alkoxy, $C_{1-4}$ alkyl, $C_{1-3}$ dialkylamino, $CF_3$, $C_{1-3}$ alkylamino, N-pyrrolidino, N-piperidino, prop-2-ene-1-oxy or 2,2,2-tri-haloethoxy;
  (b) disubstituted phenyl wherein said substituents are the same and are selected from fluoro, chloro, $C_{1-3}$ alkoxy, $C_{1-3}$ dialkylamino, N-pyrrolidino, N-piperidino, 2,2,2-trihaloethoxy, prop-2-ene-1-oxy, or the disubstituents together form a methylene dioxy group;
  (c) disubstituted phenyl wherein said substituents are not the same and are independently selected from fluoro, chloro, $C_{1-3}$ alkylamino, $C_{1-3}$ dialkylamino, N-pyrrolidino, or N-piperidino; or
  (d) disubstituted phenyl wherein one of said substituents must be $C_{1-3}$ alkoxy, 2,2,2-trihaloethoxy or prop-2-ene-1-oxy and the other substituent is independently selected from fluoro, chloro, $C_{1-3}$ alkylamino, $C_{1-3}$ dialkylamino, N-pyrrolidino, or N-piperidino;

or a salt thereof.

A further intermediate compound used in the preparation of a compound of Formula (I) is a compound of the formula:

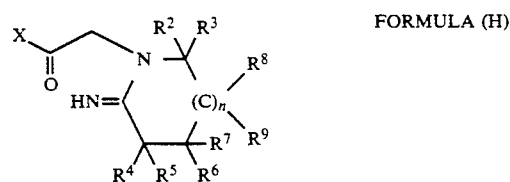

FORMULA (H)

wherein
n is 0 or 1;
$R^2$, $R^3$, $R^4$, $R^5$, $R^6$, $R^7$, $R^8$, and $R^9$ are H, or one or two of $R^2$, $R^3$, $R^4$, $R^5$, $R^6$, $R^7$, and $R^9$ are independently selected from H or $C_{1-2}$ alkyl;

X is selected from:
  (a) pyridyl;
  (b) monosubstituted phenyl, wherein said substituent is selected from H, halo, $C_{1-3}$ alkoxy, $C_{1-3}$ alkylthio, $C_{1-4}$ alkyl, N-($C_{1-3}$ alkanamido), $C_{1-3}$ dialkylamino, $CF_3$, N-pyrrolidino, or N-piperidino;
  (c) disubstituted phenyl wherein said substituents are the same and are selected from halo, $C_{1-3}$ alkoxy, $C_{1-3}$ alkylthio, N ($C_{1-3}$ alkanamido), $C_{1-3}$ dialkylamino, N-pyrrolidino, or N-piperidino, or the disubstituents together form a methylenedioxy group;
  (d) disubstituted phenyl wherein said substituents are not the same and are independently selected from halo, nitro, N-($C_{1-3}$ alkanamido), $C_{1-3}$ alkoxy, $C_{1-3}$ dialkylamino, N-pyrrolidino, or N-piperidino; or
  (e) disubstituted phenyl wherein one of said substituents must be $C_{1-3}$ alkoxy, $C_{1-3}$alkylthio, hydroxy, 2,2,2-trihaloethoxy or prop-2-ene-1-oxy and the other substituent is independently selected from halo, nitro, N-($C_{1-3}$ alkyl)-N-($C_{1-3}$ alkanamido), $C_{1-3}$ dialkylamino, N-pyrrolidino or N-piperidino; or a salt thereof.

Compounds of Formula (B), wherein n, $R^2$, $R^3$, $R^4$, $R^5$, $R^6$, $R^7$, $R^8$ and $R^9$ are as defined above, can be prepared by 0-alkylation of the corresponding 2-piperidone or 2-pyrrolidone of Formula (A), wherein n, $R^2$, $R^3$, $R^4$, $R^5$, $R^6$, $R^7$, and $R^9$ are as defined above, with an alkylating agent, such as dimethylsulfate, according to the method of Wick et al., *Helv. Chim Acta*, 54, 513 (1971). The necessary compounds of Formula (A) are commercially available or are prepared by known techniques. Compounds of Formula (C) wherein n, $R^2$, $R^3$, $R^4$, $R^5$, $R^6$, $R^7$, $R^8$, and $R^9$ are as defined above, can be prepared by treatment of the corresponding compound of Formula (B) with ammonia or an ammonium salt, such as ammonium chloride, in absolute ethanol according to the method of Etienne et al., *Compt. Rend.*, 259, 2660 (1964). Compounds of Formula (C) wherein n is 0 or 1 and $R^2$, $R^3$, $R^4$, $R^5$, $R^6$, $R^7$, $R^8$ and $R^9$ are H are preferably prepared as described by the method of Moriconia and Cevasco, *J. Org. Chem.*, 33, 2109 (1968) as their hydrohalidesalts and liberated to the bases with concentrated aqueous NaOH or preferably with one molar equivalent of sodium methoxide in an alcoholic solvent. Compounds of Formula (D), wherein $X^3$ is Br and X is as defined above, are commercially available or are prepared by treatment of the correspondingly substituted acetophenone in $CH_2Cl_2$, $CHCl_3$, acetic acid or 48% hydrobromic acid with one equivalent of bromine [See, Langley, *Org. Syn. Coll.*, 1, 127 (1944); Cowper et al., *Org. Syn. Coll.*, 2, 480 (1943); and Lorenzin, et al., *J. Org. Chem.*, 32, 4008 (1967)], or alternatively, by reaction in chloroform ethyl acetate with a suspension of copper (II) bromide by the method of King and Ostrum, *J. Org. Chem.*, 29, 3459 (1964).

The necessary acetophenones are commercially available or preparable by known techniques. Alternatively the Formula (D) compounds, wherein $X^3$ is chloro and X is (a) 4-monosubstituted phenyl where the substituent is selected from H, halo, $C_{1-4}$ alkyl, $C_{1-3}$ alkoxy, or (b) 3,4-disubstituted phenyl wherein the substituents are the same and are selected from $C_{1-3}$ alkoxy, or methylenedioxy, or where the substituents are independently selected from halo or $C_{1-3}$ alkoxy, can be prepared by acylating the corresponding mono- or di-substituted benzene by Friedel Crafts reaction with 2-chloroacetylchloride and $AlCl_3$, by the method of Joshi et al., *J. Heterocyclic Chem.*, 16, 1141 (1979).

Compounds of Formula (E) serve as intermediates in the preparation of the compounds of Formula (I). Preferably, compounds of Formula (E) are prepared from their corresponding compound of Formula (H). Compounds of Formula (H) serve as intermediates in the preparation of compounds of Formula (E). Compounds of Formula (H) are prepared by treatment of a solution of a substituted Formula (D) compound, such as a 2-haloacetophenone, or a 2-bromoacetyl 2, 3 or 4-pyridine, which are described by Taurins et al., *J. Heterocyclic Chem.*, 7, 1137 (1970), in a neutral, preferably nonpolar solvent with one molar equivalent of the corresponding Formula (C) compound, maintaining the temperature at or below 25° C. The resulting Formula (H) hydrohalide salts are converted to Formula (E) compounds by refluxing in water. Alternatively, compounds of Formula (E) are prepared by treatment of a solution of the 2-iminopyrrolidine or 2-iminopiperidine with a substituted 2-bromoacetophenone of Formula (D), either in a polar organic solvent, such as DMF or ethanol, or in a nonpolar chlorinated hydrocarbon, followed by removing all or most of the solvent and refluxing the residue in aqueous solution. Compounds of Formula (E) wherein X is a pyridyl optionally substituted by a $C_{1-4}$ alkyl group are prepared by treatment of a mixture of a bromoacetylpyridine and 2-iminopyrrolidine or their hydrohalide salts in a polar aprotic solvent, such as dimethylformamide, with 2 to 5 equivalents of a base, such as a metal carbonate salt.

Compounds of Formula (I) where R is phenyl or substituted phenyl, and $R^1$ is 4-pyridyl are preferably prepared in two steps by a modification of the method of Lantos et àl., European Patent Application No. 203,787 published Mar. 12, 1986. In the first step, the corresponding compound of Formula (E) is treated, preferably at 20°-25° C., with pyridine and an acyl halide, an aroylhalide, an arylalkyl haloformate ester, or an alkyl haloformate ester, such as acetyl bromide, benzoylchloride, benzyl chloroformate, or preferably ethyl chloroformate, in a solvent in which the reactants are soluble and inert to form the compound of Formula (F). Alternatively the acyl pyridinium salt can be preformed and added to the solution of the Formula (E) compound. Compounds of Formula (F) serve as intermediates in the preparation of the compounds of Formula (I). In the second step, the Formula (F) compound, a 1,4-dihydropyridine product, is deacylated and aromatized with sulfur in refluxing decalin, tetralin, p-cymene or xylene, or preferably with potassium tert.-butoxide in tert.-butanol with $O_2$ gas at reflux for 15 minutes to the afford the corresponding compound of Formula (I).

Compounds of Formula (I) wherein R or $R^1$ is alkyl substituted pyridyl can be prepared by a similar process from compounds of Formula (L). The Formula (L) compound is deacylated and aromatized with sulfur in decalin, tetralin, p-cymene or xylene or with potassium tert-butoxide in tert.-butanol with oxygen gas at reflux for 15 minutes to afford the corresponding Formula (I) compound. Compounds of Formula (L) are prepared by treatment of the Formula (I) compound with an acyl halide aroylhalide, arylalkyl haloformate ester or an alkyl haloformate ester and a $C_{1-4}$ alkyl Grignard reagent using the process of Comins, D. L., and Abdullah, A. H., *J. Org. Chem.*, Vol. 47, p. 4315 (1982).

The same Formula (E) compounds used to prepare the 4-pyridyl Formula (I) compounds are employed to prepare the 2-pyridyl and 3-pyridyl Formula (I) compounds. Treatment of the Formula (E) compounds with bromine by the procedure of Kano, *Yakugaku Zasshi*, 92, 51 (1972), results in 3-bromination to afford the 3-bromo-2-(substituted phenyl)-6,7-dihydro (5H)-pyrrolo(1,2-a)imidazoles and 3-bromo-2-(substituted phenyl)-5,6,7,8-tetrahydro-imidazo-(1,2-a)pyridines compounds of Formula (G). The compounds of Formula (G) serve as intermediates in the preparation of compounds of Formula (I). Formula (E) or Formula (G) compounds are treated with n butyl-lithium (n-BuLi) in tetrahydrofuran to afford their 3-lithio derivatives by metallation or halogen metal interchange respectively. Transmetallation of the 3-lithio compounds with $MgBr_2$ or $ZnCl_2$ to the corresponding magnesium or zinc compounds, according to the method of Negishi et al., *J. Org. Chem.*, 42, 1821, (1977), permits aryl coupling to a 2-, 3- or 4-bromopyridine or 2-, 3- or 4-iodopyridine in the presence of $PdCl_2$(1,4-bis(diphenylphosphino)butane) catalyst, a bidentate Pd (II) catalyst, using the method of Kumada et al., *Tetrahedron Letters*, 22, 5319 (1981). Alternatively the Formula (G) compounds may be coupled to the 2 or 3-metalated pyridine employing this bidentate Pd (II) catalyst, or the corresponding Ni(II) $Cl_2$ (1,2-bis(diphenylphosphino) ethane catalyst [see, Pridgen, *J. Org. Chem.*, 47, 4319 (1982)].

By either of these routes, Formula (I) compounds are obtained where $R^1$ is 2-pyridyl or 3 pyridyl.

The compounds of Formula (I) can also be prepared from Formula (E) by preparation of the trialkyltin derivative of Formula (E), designated as Formula (J). The compound of Formula (J) is prepared by treatment of the 3-lithio derivative of Formula (E) with trialkyltin chloride. The Formula (J) compound is reacted with a mixture of an aryl or heteroaryl halide, preferably iodide, or triflate, and tetrakis(triphenylphosphine)palladium in a mixture of THF (tetrahydrofuran) and HMPA (hexamethylphosphoramide) to yield a compound of Formula (I). The compounds of Formula (I) wherein either of R and $R^1$ are 2-pyridyl, 3-pyridyl or wherein R is 2-pyridyl, 3-pyridyl or 4-pyridyl are preferably made by this route. The compounds of Formula (I) wherein either or both of R and $R^1$ are alkyl substituted pyridyl are also prepared by this route. Alternatively, compounds of Formula (I) may be prepared by the analogous reaction of an aryl or heteroaryl trialkyltin compound with a mixture of a Formula (G) compound and tetrakis(triphenylphosphine)palladium under similar conditions.

Regioisomers of Formula (I) compounds where $R^1$ is substituted phenyl, or 2,3 or 4-pyridyl and R is 2, 3, and 4-pyridyl are obtained from compounds of Formula (E) where X is 2,3, or 4-pyridyl. Compounds of Formula (E) where X is 2, 3 or 4-pyridyl are prepared by treatment of a 2, 3, or 4-bromoacetylpyridine hydrobromide salt of Formula (D), wherein R is 2, 3 or 4-pyridyl [prepared as described by Taurins et al., *J. Het Chem.*, 7, 1137 (1970)] with 2-3 equivalents of the 2-iminopyrrolidine or 2-iminopiperidine by the procedure used to prepare the other compounds of Formula (E) described above. 3-Bromination, by the procedure of Kano cited above, affords the corresponding Formula (G) compounds. Metallation of the Formula (E) compounds with n-BuLi or halogen metal interchange of the Formula (G) compounds with n-BuLi, followed by transmetallation with $MgBr_2$ and coupling to the substituted halobenzene, preferably iodobenzene, or 2,3, or 4-halopyridine, preferably where halo is iodo, in the presence of the bidentate phosphine palladium or nickel complex as described above affords the desired regioisomers of Formula (I). Alternatively the metallated pyridine or substituted benzene may be coupled to the Formula (G) compounds employing the catalysts as described above.

Alternately the compounds of Formula (I) wherein R or $R^1$ is a mono or di-substituted phenyl having at least one fluoro substituent can be converted to the corresponding Formula (I) compounds having an alkylthio substituted phenyl group or a phenylthio substituted phenyl group. The fluoro substituted phenyl compound of Formula (I) is treated with 1.2 equivalents of the sodium salt of the alkylmercaptan or arylmercaptan in an aprotic polar solvent, preferably dimethylformamide.

Compounds of Formula (I) where R or $R^1$ is a mono or di-substituted phenyl having at least one $C_{1-3}$ alkylsulfinyl, $C_{1-3}$alkylsulfonyl, acyloxyalkylsulfinyl, or $C_{1-3}$alkenylsulfinyl substituent are prepared by treatment of one or more equivalents of the corresponding compound of Formula (I) where R or $R^1$ are $C_{1-3}$ alkylthiophenyl, $C_{1-3}$alkylsulfinylphenyl, acyloxyalkylthiophenyl or alkenylthiophenyl with one or more equivalents of an oxidizing agent (such as 3-chloroperbenzoic acid in an inert solvent or sodium periodate in a polar solvent such as aqueous methanol containing a mineral acid such as hydrochloric acid) per mercapto function, in an inert solvent. Compounds of Formula (I) wherein R or $R^1$ are $C_{1-3}$ alkylsulfonyl substituted phenyl are prepared by treatment of one equivalent of the corresponding $C_{1-3}$ sulfinyl Formula (1) compound with $\frac{2}{3}$ equivalent of $KMnO_4$ per sulfinyl function in aqueous acid solution by the method of Chatterway et al., *J. Chem. Soc.* 1352 (1930), or alternatively with one equivalent of a peracid.

Acetophenones substituted with a mono- or disubstituted phenyl having at least one N-($C_{1-3}$alkanamido) or N-($C_{1-3}$ alkyl)-N-($C_{1-3}$ alkanamido), and in some cases the Formula (E), and Formula (I) compounds, are prepared by acylation of the corresponding amino and N-($C_{1-3}$ alkylamino) compounds with the alkanoic acid anhydride or chloride in pyridine. Another alternative preparation of the N ($C_{1-3}$ alkyl)-N-($C_{1-3}$ alkanamido) phenyl substituted Formula (E) and Formula (I) compounds is the alkylation of the corresponding N ($C_{1-3}$ alkanamido) substituted compounds with sodium hydride and a $C_{1-3}$ alkyl bromide or iodide in dimethyl formamide.

Formula (E) and Formula (I) compounds containing a mono- or di substituted phenyl having at least one amino substituent are prepared either by hydrolysis of the corresponding N-($C_{1-3}$ alkanamido) compounds in refluxing 6 N mineral acid or by catalytic reduction of the corresponding nitro compounds.

Formula (E), Formula (G), and Formula (I) compounds containing a mono or di substituted phenyl having at least one N-($C_{1-3}$ alkylamino) substituent are preferably prepared by acid catalyzed hydrolysis of the corresponding N ($C_{1-3}$ alkyl)-N-($C_{1-3}$ alkanamido) compounds of Formula (E), Formula (G) and Formula (I), respectively, prepared as described above for the aminophenyl substituted compounds, or alternatively, either by (a) reduction of the corresponding N-($C_{1-3}$ alkanamido) compounds with borane or borane dimethylsulfide complex in THF by the method of Brown, "Organic Synthesis via Boranes", John Wiley and Sons, (1975), or (b) by cleavage of the corresponding N,N-(di $C_{1-3}$ alkylamino)phenyl substituted Formula (E) and Formula (I) compounds with cyanogen bromide in the Von Braun reaction [see, Hageman Org. Reactions, Vol. 7, 198 (1953)].

Formula (E) and Formula (I) compounds containing a mono- or di- substituted phenyl having at least one N,N-(di $C_{1-3}$ alkylamino) substituent are alternatively prepared either by reduction of the corresponding N-($C_{1-3}$ alkyl)-N-($C_{1-3}$ alkanamido) compounds of Formula (E) and Formula (I) with borane as described above for the N-($C_{1-3}$ alkylamino) substituted compounds, or by displacement of the bromide by a N,N dialkylamine in the corresponding 4-bromo-3-nitrophenyl Formula (E) and Formula (I) compounds by heating at 140° C. with the N,N-dialkylamine and potassium carbonate in an inert solvent.

Formula (E) and Formula (1) compounds containing a mono- or di-substituted phenyl having at least one N-pyrrolidino and N-piperidino substituent are alternatively prepared by cyclodialkylation of the corresponding aminophenyl compounds with dibromobutane or dibromopentane and anhydrous potassium carbonate in an inert solvent such as dimethylformamide.

Compounds of Formula (E) where X is mono or di-substituted phenyl having at least one 2,2,2-trihaloethoxy or prop-2-ene-1-oxy substituent are prepared by alkylation of the appropriate phenols of Formula (E) with trifluoromethylsulfonic acid 2,2,2-trifluoroethyl ester or allyl bromide respectively as described by Bender et al., *J. Med. Chem.*, 28, 1169 (1985), for preparation of compounds No. 23 and 33 described therein. Appropriately substituted mono and dihydroxy phenyl compounds or disubstituted phenyl compounds wherein one substituent is hydroxy of Formula (E) and Formula (I) are obtained by treatment of their respective correspondingly substituted methoxy derivatives with HBr in acetic acid, or preferably with $BBr_3$ in $CH_2Cl_2$ by the method described by Bender et al., *J. Med. Chem.*, 28, 1169 (1985),for the preparation of compound No. 14 described therein.

Compounds of Formula (I) where R is $C_{1-3}$alkoxy mono- or di- substituted phenyl are prepared by alkylation of the appropriately substituted hydroxyphenyl compounds with the corresponding $C_{1-3}$ alkylhalide in the presence of a strong base such as sodium hydride in an aprotic organic solvent such as dimethylformamide.

Compounds of Formula (I) wherein R or $R^1$ is phenyl substituted with an acyloxyalkylthio group wherein the alkyl is optionally substituted with $C_{1-4}$alkyl are prepared by treating a compound of Formula (I) wherein $R^1$ is phenyl substituted with at least one alkylsulfinyl group with an alkanoic acid anhydride. Hydrolysis of the resulting acyloxyalkylthio compounds yields compounds of Formula (I) wherein one of $R^1$ or R is phenyl substituted with a sulfhydryl function. The sulfhydryl substituted compounds can be treated with an alkanoic acid anhydride or a dithioalkanoic acid anhydride in pyridine to prepare compounds of Formula (I) wherein one of $R^1$ or R is phenyl substituted with one or more acylthio or dithioacyl groups.

Compounds of Formula (I) wherein one of $R^1$ or R is phenyl substituted with at least one thiocarbamyl or dithiocarbamyl group are prepared by treating the sulfhydryl-containing compound prepared as above with a carbamyl halide or thiocarbamyl halide in the presence of a base such as pyridine to yield the desired compounds.

Compounds of Formula (I) wherein $R^1$ or R is phenyl substituted with an alkenylthio group wherein one carbon atom separates the sulfur from the carbon bearing the double bond can be prepared by alkylating a compound of Formula (I) wherein one of $R^1$ or R is phenyl substituted with at least one sulfhydryl group with an appropriately substituted alkenylhalide, such as allylbromide.

Compounds of Formula (I) wherein $R^1$ or R is phenyl substituted with an alkylcarbonylalkylthio or carbalkoxyalkylthio group are prepared by treatment of the corresponding sulfhydryl substituted compounds with an alkylcarbonylalkylhalide, such as bromoacetone, or with a carbalkoxyalkylhalide, such as ethylbromoacetate.

Compounds of Formula (I) wherein R or $R^1$ is phenyl substituted with an alkenylthio group wherein the sulfur is attached to the carbon bearing the double bond are prepared from the corresponding compounds wherein the phenyl is substituted with a mercapto group. The mercapto substituted compound is converted to a metal salt in a polar solvent with a strong base such as a metal hydride, a metal alkoxide or lithium diethylamide. The metal mercaptide salt is treated with trialkylsilylmethylchloride to afford an intermediate compound of Formula (I) wherein R or $R^1$ is phenyl substituted with at least one trialkylsilylmethylsulfide group. This intermediate in an aprotic solvent such as tetrahydrofuran is treated at reduced temperature with a lithiating reagent such as lithium diethylamide followed by treatment with an appropriate aliphatic aldehyde or ketone to prepare the compounds of Formula (I) wherein R or $R^1$ is phenyl substituted with one or more alkenylthio groups.

Compounds of Formula (I) wherein R or $R^1$ is phenyl substituted with an alkoxycarbonylthio are prepared by reacting a metal mercaptide salt prepared as described above, with an appropriate alkyl or aryl chloroformate. The metal mercaptide salt is formed from a compound of Formula (I) wherein one of R or $R^1$ is phenyl substituted with a sulfhydryl function prepared as previously described. Compounds of Formula (I) wherein R or $R^1$ is phenyl substituted with one or more alkoxythionothio groups are prepared by reacting the metal mercaptide with the appropriate alkyl or aryl halothionoformate.

Compounds of Formula (I) wherein R or $R^1$ is alkoxyalkylthio are prepared by reacting the metal mercaptide salt, prepared as described above, with an appropriate halomethyl ether. Oxidation of the resulting alkoxyalkylthio compounds by reacting with a suitable oxidizing agent such as chloroperbenzoic acid yields the compounds of Formula (I) wherein R or $R^1$ is phenyl substituted with an alkoxyalkylsulfinyl.

Compounds of Formula (I) wherein R or $R^1$ is phenyl substituted with an alkylthioalkylthio group are prepared by reacting the analogous sulfhydryl compound, prepared as described above, with the appropriate carbonyl component using either mineral or Lewis acid catalysis to yield the symmetrical dithioketal. The nonsymmetrical thioketals can be prepared by the reaction of the metal mercaptan salt, prepared as described above, with a halomethyl thioether to yield compounds of Formula (I) wherein one of R or $R^1$ is phenyl substituted with one or more alkylthioalkylthio groups.

Compounds of Formula (I) wherein R or $R^1$ is phenyl substituted with a substituted disulfide group are prepared by mild air oxidation of the compounds of Formula (I) wherein R or $R^1$ is phenyl substituted with a sulfhydryl group, prepared as described above. The nonsymmetrical disulfide compound may be prepared by reaction of the sulfhydryl compound with the appropriate sulfenyl halide in an ethereal solvent to afford compounds of Formula (I) wherein one of R or $R^1$ is phenyl substituted with one or more alkyldithio groups.

Pharmaceutically acceptable salts and their preparation are well known to those skilled in pharmaceuticals. Pharmaceutically acceptable salts of the compounds of Formula (I) which are useful in the present invention include, but are not limited to, maleate, fumarate, lactate, oxalate, methanesulfonate, ethane-sulfonate, benzenesulfonate, tartrate, citrate, hydrochloride, hydrobromide, sulfate and phosphate salts. Preferred pharmaceutically acceptable salts of the compounds of Formula (I) include hydrochloride and hydrobromide salts, and such salts can be prepared by known techniques such as the method of Bender et al., U.S. Pat. No. 4,175,127, the disclosure of which is hereby incorporated by reference.

It has now been discovered that the compounds of Formula (I) are useful for treating disease states mediated by the 5-lipoxygenase pathway of arachidonic acid metabolism in an animal, including mammals, in need thereof. The discovery that the compounds of Formula (I) are inhibitors of the 5-lipoxygenase pathway is based on the effects of the compounds of Formula (I) on tissue inflammation in vivo and on the production of 5-lipoxygenase products by inflammatory cells in vitro in assays, some of which are described hereinafter. In summary, such assays reveal that the compounds of Formula (I) display anti-inflammatory activity in arachidonic acid-induced inflammation in the mouse ear model. The cyclooxygenase inhibitor, indomethacin, did not reduce inflammation in these assays. The 5-lipoxygenase pathway inhibitory action of the compounds of Formula (I) was confirmed by showing that they impaired the production of 5-lipoxygenase products such as leukotriene B$_4$ (di-HETE) and 5-HETE production by RBL-1 cells.

The pathophysiological role of arachidonic acid metabolites has been the focus of recent intensive studies. In addition to the well-described phlogistic activity (i.e. general inflammatory activity) of prostaglandins, the more recent description of similar activity for eicosanoids has broadened the interest in these products as mediators of inflammation [See, O'Flaherty, Lab. Invest., 47, 314–329 (1982)]. The reported discovery of potent chemotactic and algesic activity for LTB$_4$ [see, Smith, Gen. Pharmacol., 12, 211–216 (1981) and Levine et al., Science, 225, 743–745 (1984)], together with known LTC$_4$ and LTD$_4$-mediated increase in capillary permeability [see, Simmons et al., Biochem. Pharmacol., 32, 1353–1359 (1983), Veno et al., Prostaglandins, 21, 637–647 (1981), and Camp et al., Br. J. Pharmacol., 80, 497–502 (1983)], has led to their consideration as targets for pharmacological intervention in both the fluid and cellular phases of inflammatory diseases.

The pharmacology of several inflammatory model systems has attested to the effectiveness of corticosteroids in reducing the cellular infiltration. These results, and the observation that corticosteroids inhibit the generation of both cyclooxygenase and lipoxygenase products, suggest that dual inhibitors may effectively reduce both the fluid and cellular phases of the inflammatory response since selective cyclooxygenase inhibitors do not reliably inhibit cell influx into inflammatory sites [See, Vinegar et al , Fed. Proc., 35, 2447–2456 (1976), Higgs et al., Brit. Bull., 39, 265–270 (1983), and Higgs et al., Prostaglandins, Leukotrienes and Medicine, 13, 89–92 (1984)]. The observations outlined above cogently argue that a dual inhibitor of arachidonic acid metabolism would be a more effective antiinflammatory agent than an inhibitor of cyclooxygenase only. Under optimal conditions, it is likely that an agent with preferential lipoxygenase inhibitory activity would not share the ulcerogenic liability of cyclooxygenase inhibitors or the toxicity of corticosteroids. This may suggest that the compounds of the present invention could be useful in treating diseases where it is beneficial to limit ulcerogenic activity or steroidal side effects such as osteoarthritis. [See Palmoski et al., "Benoxaprofen Stimulates Proteoglycan Synthesis in Normal Canine Knee Cartiledge in Vitro," Arthritis and Rheumatism 26, 771–774 (1983) and Rainsford, K. D., Agents and Actions 21, 316–319 (1987).]

Recent clinical data also support the enthusiasm for inhibitors of the 5-lipoxygenase pathway in a variety of inflammatory diseases in which granulocyte and/or monocyte infiltration is prominent. The reported demonstration of elevated levels of LTB$_4$ in rheumatoid arthritic joint fluid [See, Davidson et al., Ann. Rheum. Dis., 42, 677–679 (1983)] also suggests a contributing role for arachidonic acid metabolites in rheumatoid arthritis. The recently reported preliminary observation of efficacy, including remission, reported with sulfasalazine treatment of rheumatoid arthritic patients See Neumann et al., Brit. Med. J., 287, 1099–1102 (1983)] illustrates the utility of inhibitors of the 5-lipoxygenase pathway in rheumatoid arthritis.

Sulfasalazine, which is used for treatment of ulcerative colitis, has been reported to inhibit LTB$_4$ and 5-HETE production in vitro [See, Stenson et al., J. Clin. Invest., 69, 494–497 (1982)]. This observation, coupled with the fact that it has been reported that inflamed gastrointestinal mucosa from inflammatory bowel disease patients showed increased production of LTB$_4$ [See, Sharon et al., Gastroenterol., 84, 1306 (1983)], suggests that sulfasalazine can be effective by virtue of inhibition of production of chemotactic eicosanoids (such as the 5-lipoxygenase pathway product known as LTB$_4$). The observations serve to underscore utility of inhibitors of the 5-lipoxygenase pathway in inflammatory bowel disease.

Another area of utility for an inhibitor of the 5-lipoxygenase pathway is in the treatment of psoriasis. It was demonstrated that involved psoriatic skin had elevated levels of LTB$_4$ [See, Brain et al., Lancet, 19, Feb. 19, 1983]. The promising effect of benoxaprofen on psoriasis [See, Allen et al., Brit. J. Dermatol., 109, 126–129 (1983)], a compound with in vitro lipoxygenase inhibitory activity on psoriasis, lends support to the concept that inhibitors of the 5-lipoxygenase pathway can be useful in the treatment of psoriasis.

Lipoxygenase products have been identified in exudate fluids from gouty patients. This disorder is characterized by massive neutrophil infiltration during the acute inflammatory phases of the disease. Since a major 5-lipoxygenase product, LTB$_4$, is produced by neutrophils, it follows that inhibition of the synthesis of LTB$_4$ can block an amplification mechanism in gout.

Another area in which inhibitors of the 5-lipoxygenase product can have utility is in myocardial infarction. Studies in dogs with the dual inhibitor, BW755-C, demonstrated that the area of infarction following coronary occlusion was reduced, and such reduction was attributed to inhibition of leukocyte infiltration into the ischaemic tissue [See, Mullane et al., J. Pharmacol. Exp. Therap., 228, 510–522 (1984)].

Yet another area of utility for inhibitors of the 5-lipoxygenase pathway is in the area of prevention of rejection of organ transplants. [See, e.g., Foegh et al., Adv. Prostaglandin, Thromboxane, and Leukotriene Research, 13, 209–217 (1983).]

Yet another utility for inhibitors of the 5-lipoxygenase pathway is in the treatment of tissue trauma. [See, e.g., Denzlinger et al. Science, 230 (4723), 330–332 (1985)].

Furthermore, another area of utility for inhibitors of the 5-lipoxygenase pathway is in the treatment of inflammatory reaction in the central nervous system, including multiple sclerosis. [See, e.g., Mackay et al., Clin. Exp. Immunology, 15, 471–482 (1973)].

Additionally, another area of utility for inhibitors of the 5-lipoxygenase pathway is in the treatment of asthma. [See, e.g., Ford-Hutchinson, J. Allergy Clin. Immunol., 74, 437–440 (1984)].

Another area of utility for inhibitors of the 5-lipoxygenase pathway is in the treatment of vasculitis, glomerulonephritis, and immune complex disease. [See Kadison et al., "Vasculitis: Mechanism of Vessel Damage" in Inflammation: Basic Principles and Clinical Correlates, 703–718, Ed. Gallin et al., Raven Press, N.Y., N.Y. (1988).]

Another area of utility for inhibitors of the 5-lipoxygenase pathway is in the treatment of dermatitis. [See Pye et al., "Systemic Therapy" in Textbook of Dermatology, Vol. III, 2501–2528, Ed. Rook et al., Blackwell Scientific Publications, Oxford, England (1986).]

Another area of utility for inhibitors of the 5-lipoxygenase pathway is in the treatment of atherosclerosis. Recent studies have shown that inhibition of oxidative modification of low density lipoprotein slows progression of atherosclerosis, and that inhibitors of lipoxygenase effectively inhibit cell induced oxidative modification. [See Carew et al., *Proc. Natl. Acad. Sci. U.S.A.*, 84, 7725–7729, November 1987; and Steinberg, D., *Cholesterol and Cardiovascular Disease*, 76, 3, 508–514(1987).]

An additional area of utility for inhibitors of the 5-lipoxygenase pathway is in the optical area, in particular general inflammation of the corneal anterior and posterior segments due to disease or surgery such as in post surgical inflammation, uveitis, and allergic conjunctivitis. [See Rao N. et al. *Arch. Ophathmal.* 105 (3) 413–419 (1987); Chiou, L. and Chiou, G. *J. Ocular Pharmacol.* 1, 383–390 (1985); Bazan H., *J. Ocular Pharma.* 4, 43–49 (1988); and Verbey N. L. et al., *Current Eye Research* 7, 361–368 (1988).]

The pharmaceutically effective compounds of this invention are administered in conventional dosage forms prepared by combining a compound of Formula (I) ("active ingredient") in an amount sufficient to produce 5-lipoxygenase pathway inhibiting activity with standard pharmaceutical carriers according to conventional procedures. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

To obtain a stable water soluble dose form, a pharmaceutically acceptable salt of a compound of Formula (I) is dissolved in an aqueous solution of an organic or inorganic acid, such as a 0.3 M solution of succinic acid or, preferably, citric acid.

Preferably, each parenteral dosage unit will contain the active ingredient [i.e., the compound of Formula (I)] in an amount of from about 50 mg. to about 500 mg. Preferably, each oral dosage will contain the active ingredient in an amount of from about 100 mg to about 1000 mg.

The compounds of Formula (I) may also be administered topically to a mammal in need of the inhibition of the 5-lipoxygenase pathway of arachidonic acid metabolism. Thus, the compounds of Formula (I) may be administered topically in the treatment or prophylaxis of inflammation in an animal, including man and other mammals, and may be used in the relief or prophylaxis of 5-lipoxygenase pathway mediated diseases such as rheumatoid arthritis, rheumatoid spondylitis, osteoarthritis, gouty arthritis and other arthritic conditions, inflamed joints, eczema, psoriasis or other inflammatory skin conditions such as sunburn; inflammatory eye conditions including conjunctivitis; pyresis, pain and other conditions associated with inflammation.

The amount of a compound of Formula (I) (hereinafter referred to as the active ingredient) required for therapeutic effect on topical administration will, of course, vary with the compound chosen, the nature and severity of the inflammatory condition and the animal undergoing treatment, and is ultimately at the discretion of the physician. A suitable anti-inflammatory dose of an active ingredient is 1.5 µg to 500 mg of base for topical administration, the most preferred dosage being 1 µµg to 1000 µg, for example 5 to 25 µg administered two or three times daily.

By topical administration is meant non-systemic administration and includes the application of a compound of Formula (I) externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as: liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as qlycerol or an oil such as castor oil or arachis oil.

Creams, ointments or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as steric or oleic acid together with an alcohol such as propylene glycol or macrogols. The formulation may incorporate any suitable surface active agent such as an anionic, cationic or non-ionic sulfactant such as sorbitan esters or polyoxyethylene derivatives thereof. Suspending agents such as natural gums, cellulose derivatives or inorganic materials such as silicaceous silicas, and other ingredients such as lanolin, may also be included.

The compounds of Formula (I) may also be administered by inhalation. By "inhalation" is meant intranasal and oral inhalation administration. Appropriate dosage forms for such administration, such as an aerosol formulation or a metered dose inhaler, may be prepared by conventional techniques. The preferred daily dosage amount of a compound of Formula (I) administered by inhalation is from about 10 mg to about 100 mg per day.

This invention also relates to a method of treating a disease state which is mediated by the 5-lipoxygenase pathway in an animal in need thereof, including humans and other mammals, which comprises administering to such animal an effective, 5-lipoxygenase pathway inhibiting amount of a Formula (1) compound. By the term "treating" is meant either prophylactic or therapeutic therapy. By the term "mediated" is meant caused by or exacerbated by. Such Formula (I) compound can be administered to such animal in a conventional dosage form prepared by combining the Formula (I) compound with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well known variables. The Formula (I) compound is administered to an animal in need of inhibition of the 5-lipoxygenase pathway in an amount sufficient to inhibit the 5-lipoxygenase pathway. The route of administration may be oral, parenteral, by inhalation or topical. The term parenteral as used herein includes intravenous, intramuscular, subcutaneous, intrarectal, intravaginal or intraperitoneal administration. The subcutaneous and intramuscular forms of parenteral administration are generally preferred. The daily parenteral dosage regimen will preferably be from about 50 mg to about 1000 mg per day. The daily oral dosage regimen will preferably be from about 150 mg to about 2000 mg per day. It will be recognized by one of skill in the art that the optimal quantity and spacing of individual dosages of the Formula (I) compound will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of the Formula (I) compound given per day for a defined number of days, can be ascertained by those skilled in the art using conventional course of treatment determination tests.

In the tests used to determine activity as 5-lipoxygenase pathway inhibitors, male Balb/c mice (20–28 g), were used. All mice were obtained from Charles River Breeding Laboratories, Kingston, N.Y. Within a single experiment, mice were age matched.

Reagents were employed as follows:
Compounds of Formula (I) were each used as the free base. The compounds were dissolved in acid saline. Compounds were administered by lavage at the indicated dose in a final volume of 10 ml/kg.

For in vitro experiments, compounds were dissolved concentrations in ethanol (final concentration 1.0%) and then diluted to final concentrations using the buffers indicated in the text.

ARACHIDONIC ACID-INDUCED MOUSE EAR INFLAMMATION

Arachidonic acid in acetone (2 mg/20 μl) was applied to the inner surface of the left ear. The thickness of both ears was then measured with a dial micrometer one hour after treatment, and the data were expressed as the change in thickness ($10^{-3}$ cm) between treated and untreated ears.

Test compounds were given orally in acid/saline at the times indicated in the text prior to the topical application of arachidonic acid.

ASSAY OF 5-LIPOXYGENASE ACTIVITIES

The 5-lipoxygenase (5LO) was isolated from extracts of RBL-1 cells. These cells were obtained from the American Type Culture Collection (#CRL 1378) and were grown at 37° with 5% $CO_2$ in spinner culture using Eagles essential medium (MEM) supplemented medium with 10% heat inactivated fetal calf serum. The cells were collected from culture by centrifugation at 2,000 xg for 20 minutes and then washed twice with 50 mM sodium phosphate (pH 7.0) that contained 1 mM EDTA and 0.1% gelatin. After this wash, the cells were resuspended in fresh phosphate buffer to achieve a concentration of $5 \times 10^7$ cells/ml. This suspension was disrupted by nitrogen cavitation using the Parr bomb at 750 psi for 10 minutes. The broken cells were then centrifuged at 10,000 xg for 20 minutes. The supernatant was collected and centrifuged at 100,000 xg for 60 minutes. This supernatant was collected and stored at $-70°$ C. until assayed.

The inhibition of 5-lipoxygenase activity was measured by one of two assays, the radiotracer extent assay either measured after 90 seconds at 20° C. or measured according to the method of G. K. Hogaboom et al., *Molecular Pharmacol.* 30, 510–519 (1986) or the continuous $O_2$ consumption assay. The results from either assay are comparable if not identical. All compounds were dissolved in ethanol with the final concentration of ethanol being 1% in the assay.

The radiotracer extent assay examined the 5-lipoxygenase products [transLTB$_4$ (DI-HETE), 5HETE and 5HPETE] produced after a 90 second incubation at 20° C. Aliquots (40 μL) of the supernatant were preincubated with the inhibitor or vehicle for 10 minutes in 25 mM BisTris buffer (pH 7.0) that also contained 1 mM EDTA. 1 mM ATP, 50 mM NaCl, 5% ethylene gylcol and 100 μg/ml of sonicated phosphatidylcholine (total volume 0.238 ml). The 5-lipoxygenase reaction was initiated by the addition of CaCl$_2$ (2 mM) and 1-C14-arachidonic acid (25 μM; 100,000 dpm))(final volume 0.25 ml). After 90 seconds, the reaction was terminated by the addition of two volumes (0.5 ml) of ice chilled acetone. The sample was allowed to deproteinize on ice for 10 minutes prior to centrifuging at 1,000 xg for 10 minutes. The deproteinized supernatants were dried under argon and then redissolved in 200 μL of ethanol. These samples were then analyzed by reverse phase HPLC as described by G. K. Hogaboom et al., *Molecular Pharmacol.* 30: 510–519 (1986), herein incorporated by reference. The compound-mediated inhibition of 5-lipoxygenase activity is described as the concentration of compound causing a 50% inhibition of product synthesis.

The second assay for assessing inhibition of the 5-lipoxygenase activity was a continuous assay which monitored the consumption of O$_2$ as the reaction progressed. The 5-lipoxygenase enzyme (200 μL) was preincubated with the inhibitor or its vehicle in 25 mM BisTris buffer (pH 7.0) that contained 1 mM EDTA, 1 mM ATP, 5 mM NaCl and 5% ethylene glycol for 2 minutes at 20° C. (total volume 2.99 ml). Arachidonic acid (10 μM) and CaCl$_2$ (2 mM) were added to start the reaction, and the decrease in O$_2$ concentration followed with time using a Clark-type electrode and the Yellow Spring O$_2$ monitor (type 53)(Yellow Springs, Oh.). The optimum velocity was calculated from the progress curves. The compound-mediated inhibition of 5-lipoxygenase activity is described as the concentration of compound causing a 50% inhibition of optimum velocity for the vehicle treated sample.

LTC-4 PRODUCTION FROM HUMAN MONOCYTES IN VITRO

Human monocytes were prepared from leukosource packs supplied by the American Red Cross. The leukosource packs were fractionated by a two-step procedure described by F. Colatta et al., *J. Immunol.* 132, 936 (1984), herein incorporated by reference, that uses sedimentation on Ficoll followed by sedimentation on Percoll. The monocyte fraction that results from this technique was composed of 80–90% monocytes with the remainder being neutrophils and lymphocytes.

The monocytes (1.5×10$^6$) were placed into polypropylene tubes and used as a suspended culture. The assay buffer consisted of RPMI 1640 buffer, [Moore, G. E. et al., JAMA, 199, 519 (1967) herein incorporated by reference] 1% human AB serum, 2 mM glutamine, 25 mM HEPES [4-(2-hydroxyethyl) 1-piperazine-ethanesulfonic acid], and 1 mM CaCl$_2$ (total volume 0.45 ml). Compounds (0.05 ml) were added in 10% ethanol solution, and the cells were preincubated for 45–60 minutes at 37° C. with constant agitation. A23187 calcium ionophore (2 μM) was used to stimulate the cells. After an additional 15 minutes, the buffer was collected by centrifugation (600 xg for 15 minutes) and stored at −70° C. until assayed. LTC$_4$ production was measured by radioimmunassay which was performed using a New England Nuclear Leukotriene C-4($^3$H) RIA Kit according to the manufacturer's (New England Nuclear, Boston, Mass.) instructions. The compound-mediated inhibition of LTC$_4$ is described as the concentration of compound causing a 50% inhibition of LTC$_4$ production.

INHIBITION OF THE EICOSANOID PRODUCTION FOLLOWING CALCIUM IONOPHORE (60 μM) STIMULATION IN HUMAN WHOLE BLOOD

The eicosanoids, which include the 5-lipoxygenase products LTB$_4$, transLTB$_4$, 20-hydroxyLTB$_4$, 5-HETE, and the 12-lipoxygenase product are extracted from the whole blood following A23187 calcium ionophore stimulation. The extracts are separated by reverse phase high pressure liquid chromatography and quantified by absorbance methods.

Venous human blood is collected into polypropylene tubes containing 1% heparin. The blood is then aliquoted into 4.5 ml volumes and preincubated at 37° C. for 10 minutes in polypropylene tubes (15 ml size). Compound or carrier (50 μL dimethylsulfoxide) is added 5 minutes prior to stimulation. Calcium ionophore (0.5 ml) is added, and the blood incubated for 10 minutes. Prostaglandin B$_2$(1 nmole) is added, and the blood extracted as described below.

The samples are centrifuged at 1000 xg for 15 minutes at 5° C. The plasma is collected, and one volume of methanol is added to the plasma. This suspension is then centrifuged at 1000 xg for ten minutes at 5° C. The supernatant is collected and diluted with 1.5 volumes of chilled aqueous 1% formic acid: 1% triethylamine. This mixture is loaded onto a preconditioned J. T. Baker C18 SPE cartridge (Phillipsburg, N.J.) at a flow rate of 1–2 ml/minute. (The cartridge is preconditioned according to manufacture's recommendations.) The absorbed sample is washed in the following order with three (3) ml each of (i) aqueous 1% formic acid: 1% triethylamine; (ii) petroleum ether; and (iii) 20% acetonitrile: 1% triethylamine.

The eicosanoids are eluted in 3 ml of 70% acetonitrile: 1% triethylamine. The solvent is removed under vacuum. The sample is resuspended in 200 μL of 50% methanol buffered with ammonium acetate.

The sample (175 μl) is loaded into a WATERS (Milford, Mass.) RCM NOVA PAK C18 (100×8 mm) column with the starting mobile phase of 90% A (A=10% acetonitrile buffered with 30 mM ammonium acetate to pH 6.8) and 10% B (B=90% acetonitrile buffered with 30 mM ammonium acetate to pH6.8). The flow rate for the separation is 2.5 ml/minute. At one minute the %B is increased to 27% in a step fashion. By 12 minutes the %B has increased in a concave hyperbolic function (curve 9) to 40% and increases in a linear manner to 60% by 22 minutes. Under these developing conditions, the retention times for the eicosanoids are: 20-hydroxyLTB$_4$, 4.6 minutes; thromboxane B$_2$, 6.5 minutes; transLTB$_4$, 10 minutes; LTB$_4$, 10.5 minutes; 12-HETE, 10.4 minutes; 5-HETE, 21 minutes. The HPLC system consisted of WATERS 510 pumps, 840 controller, WISP injector and 990 detector.

The eicosanoids in the samples are verified by their retention times and their UV absorbance spectra. The peaks are quantified with reference to the internal standard and their absorbance response at their maximum absorbance wavelength.

THE EFFECT OF COMPOUNDS OF FORMULA (I) ON ARACHIDONIC ACID-INDUCED INFLAMMATION

Elucidation of the antiinflammatory activity of the compounds of Formula (I) was achieved in a model of arachidonic acid-induced edema in mice. The mouse ear edematous response to arachidonic acid has been shown to be sensitive to agents that inhibit both lipoxygenase- and cyclooxygenase-generated mediators or that selectively inhibit lipoxygenase, but not cyclooxygenase, enzyme activity [See, Young et al., J. Invest. Dermatol., 82, 367-371 (1984)]. Compounds of Formula (I) produced marked inhibition of the edematous response normally seen 1 hour after the application of 2 mg of arachidonic acid to the ear (Table I). The cyclooxygenase inhibitors, indomethacin (10 mg/kg, p.o.), ibuprofen (250 mg/kg, p.o.) and naproxen (100 mg/kg, p.o.) do not exhibit detectable antiinflammatory activity in this assay.

These findings indicate that compounds of Formula (I) are potent inhibitors of both the cellular and edematous responses of inflammation in mice. These inflammatory responses were also inhibited by agents that inhibit lipoxygenase activity but not by selective cyclooxygenase inhibitors.

THE EFFECT OF COMPOUNDS OF FORMULA (I) ON ARACHIDONIC ACID METABOLISM

Experiments using a soluble extract preparation of RBL-1 cells containing only lipoxygenase activity confirmed the inhibitory effects of compounds of Formula (I) on $LTB_4$ (DI-HETE) production (Table II). Indomethacin at concentrations up to $10^{-4}M$ was inactive. The data presented in Table II indicate that compounds of Formula (I) are inhibitors of the 5-lipoxygenase pathway as confirmed by their ability to inhibit DI-HETE, a 5-lipoxygenase pathway product. The data presented in Table III indicate that compounds of Formula (I) are inhibitors of the 5-lipoxygenase pathway as confirmed by their ability to inhibit the total 5-HETE and DI-HETE, 5-lipoxygenase pathway products. The data in Table IIIA indicates that compounds of Formula (I) are inhibitors of the 5-lipoxygenase pathway as confirmed by measurement of oxygen consumption by the 5-lipoxygenase enzyme.

$LTC_4$ INHIBITION ASSAY

As shown in Table IV, compounds of Formula (I) were efficacious in inhibiting $LTC_4$ production, a 5-lipoxygenase pathway product, by human monocytes. These data confirm the ability of compounds of Formula (I) to inhibit the 5-lipoxygenase pathway.

INHIBITION OF EICOSANOID PRODUCTION

As shown in Table V, compounds of Formula (I) were effective in inhibiting the production of various 5-lipoxygenase pathway products in human blood. This data demonstrates that the compounds of Formula (I) inhibit the 5-lipoxygenase pathway. The inhibition of thromboxane $B_2$ demonstrates that the compounds inhibit the cyclooxygenase pathway and are therefore dual inhibitors.

TABLE I

The Effect of Compounds of Formula (I) on Archidonic Acid Induced Ear Swelling

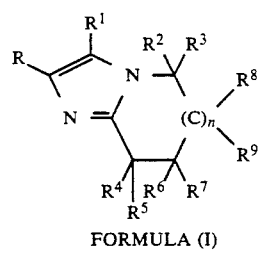

FORMULA (I)

| Compound Number | R | $R^1$ | $R^2$ | $R^3$ | $R^4$ | $R^5$ | $R^6$ | $R^7$ | $R^8$ | $R^9$ | n | % Inhibition of Ear Swelling[a,b,c] |
|---|---|---|---|---|---|---|---|---|---|---|---|---|
| 1 | 4-methylthiophenyl | 4-pyridyl | H | H | H | H | H | H | — | — | 0 | 62*** |
| 2 | 4-methylsulfinylphenyl | 4-pyridyl | H | H | H | H | H | H | — | — | 0 | 44*** p.o. |
| 3 | 4-methylsulfonylphenyl | 4-pyridyl | H | H | H | H | H | H | — | — | 0 | 3NS |
| 4 | 4-methoxyphenyl | 2-pyridyl | H | H | H | H | H | H | — | — | 0 | 29** |
| 5 | 4-methoxyphenyl | 3-pyridyl | H | H | H | H | H | H | — | — | 0 | 34** |
| 6 | 4-methoxyphenyl | 2,6-dimethyl-4-pyridyl | H | H | H | H | H | H | — | — | 0 | NT |
| 7 | 4-hydroxyphenyl | 4-pyridyl | H | H | H | H | H | H | — | — | 0 | 27***p.o. |
| 8 | 4-ethoxyphenyl | 4-pyridyl | H | H | H | H | H | H | — | — | 0 | 62***p.o. |
| 9 | 4-n-propoxyphenyl | 4-pyridyl | H | H | H | H | H | H | — | — | 0 | 42***p.o. |
| 10 | 4-isopropoxyphenyl | 4-pyridyl | H | H | H | H | H | H | — | — | 0 | 43***p.o. |
| 11 | 4-acetylthiophenyl | 4-pyridyl | H | H | H | H | H | H | — | — | 0 | 46***p.o. |
| 12 | 4-trimethylacetylthiophenyl | 4-pyridyl | H | H | H | H | H | H | — | — | 0 | 45***p.o. |
| 13 | 4-acetoxymethylthiophenyl | 4-pyridyl | H | H | H | H | H | H | — | — | 0 | 51***p.o. |
| 14 | 4-ethylthiophenyl | 4-pyridyl | H | H | H | H | H | H | — | — | 0 | 56***p.o. |
| 15 | 4-ethylsulfinylphenyl | 4-pyridyl | H | H | H | H | H | H | — | — | 0 | 41***p.o. |
| 16 | 4-carbethoxymethylthiophenyl | 4-pyridyl | H | H | H | H | H | H | — | — | 0 | 15*** |
| 17 | 4-pyridyl | H | H | H | H | H | H | H | — | — | 0 | 20p.o. 41* |
| 18 | 4-pyridyl | 4-methylthiophenyl | H | H | H | H | H | H | — | — | 0 | 28*p.o. 32* |
| 19 | 4-pyridyl | 4-methylsulfinylphenyl | H | H | H | H | H | H | — | — | 0 | 52*p.o. 56* |
| 20 | 4-methylthiophenyl | 4-(2-methyl)pyridyl | H | H | H | H | H | H | — | — | 0 | 59*p.o. 59* |
| 21 | 4-methylsulfinylphenyl | 4-(2-methyl)pyridyl | H | H | H | H | H | H | — | — | 0 | 59***p.o. 14* |

TABLE I-continued

The Effect of Compounds of Formula (I) on Arachidonic Acid Induced Ear Swelling

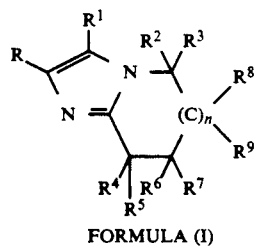

FORMULA (I)

| Compound Number | R | R¹ | R² | R³ | R⁴ | R⁵ | R⁶ | R⁷ | R⁸ | R⁹ | n | % Inhibition of Ear Swelling$^{(a,b,c)}$ |
|---|---|---|---|---|---|---|---|---|---|---|---|---|
| 22 | 4-methoxyphenyl | 4-(2-methyl)pyridyl | H | H | H | H | H | H | — | — | 0 | 56*p.o. 57* |

$^{a)}$screened at 50 mg/kg s.c. or i.p. unless indicated as oral dosing (p.o.).
$^{b)}$* = p .05,  = p .01, * = p .001, NS = not significant.
$^{c)}$NT = Not Tested

TABLE II

The Effect of Compounds of Formula (I) on 5-Lipoxygenase Activity (DI-HETE Production)

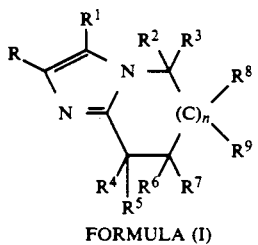

FORMULA (I)

| Compound Number | R | R¹ | R² | R³ | R⁴ | R⁵ | R⁶ | R⁷ | R⁸ | R⁹ | n | 5-LO$^{a,b}$ IC$_{50}$ (uM) |
|---|---|---|---|---|---|---|---|---|---|---|---|---|
| 1 | 4-methylthiophenyl | 4-pyridyl | H | H | H | H | H | H | — | — | 0 | 20 |
| 2 | 4-methylsulfinylphenyl | 4-pyridyl | H | H | H | H | H | H | — | — | 0 | >100 |
| 3 | 4-methylsulfonylphenyl | 4-pyridyl | H | H | H | H | H | H | — | — | 0 | >100 |
| 4 | 4-methoxyphenyl | 2-pyridyl | H | H | H | H | H | H | — | — | 0 | >100 |
| 5 | 4-methoxyphenyl | 3-pyridyl | H | H | H | H | H | H | — | — | 0 | NT |
| 6 | 4-methoxyphenyl | 2,6-dimethyl-4-pyridyl | H | H | H | H | H | H | — | — | 0 | NT |
| 7 | 4-hydroxyphenyl | 4-pyridyl | H | H | H | H | H | H | — | — | 0 | 17 |
| 8 | 4-ethoxyphenyl | 4-pyridyl | H | H | H | H | H | H | — | — | 0 | 6 |
| 9 | 4-n-propoxyphenyl | 4-pyridyl | H | H | H | H | H | H | — | — | 0 | 3.5 |
| 10 | 4-isopropoxyphenyl | 4-pyridyl | H | H | H | H | H | H | — | — | 0 | 37 |

$^{a}$IC$_{50}$ determined DI-HETE production by RBL-1 high speed supernatant.
$^{b}$NT = Not tested.

TABLE III

The Effect of Compounds of Formula (I) on 5-Lipoxygenase Activity (Total HETE and Di-HETE) Production

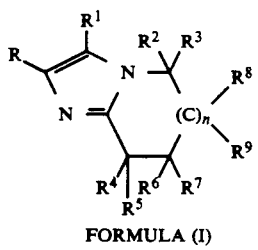

FORMULA (I)

| Compound Number | R | R¹ | R² | R³ | R⁴ | R⁵ | R⁶ | R⁷ | R⁸ | R⁹ | n | 5-LO$^{a,b}$ IC$_{50}$ (uM) |
|---|---|---|---|---|---|---|---|---|---|---|---|---|
| 1 | 4-methylthiophenyl | 4-pyridyl | H | H | H | H | H | H | — | — | 0 | 23 |
| 2 | 4-methylsulfinylphenyl | 4-pyridyl | H | H | H | H | H | H | — | — | 0 | >100 |
| 3 | 4-methylsulfonylphenyl | 4-pyridyl | H | H | H | H | H | H | — | — | 0 | >100 |
| 4 | 4-methoxyphenyl | 2-pyridyl | H | H | H | H | H | H | — | — | 0 | 35 |
| 5 | 4-methoxyphenyl | 3-pyridyl | H | H | H | H | H | H | — | — | 0 | NT |

TABLE III-continued

The Effect of Compounds of Formula (I) on 5-Lipoxygenase Activity (Total HETE and Di-HETE) Production

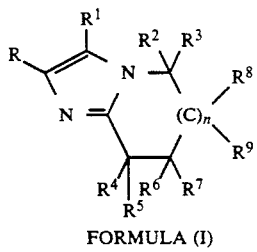

FORMULA (I)

| Compound Number | R | R¹ | R² | R³ | R⁴ | R⁵ | R⁶ | R⁷ | R⁸ | R⁹ | n | 5-LO[a,b] IC$_{50}$ (uM) |
|---|---|---|---|---|---|---|---|---|---|---|---|---|
| 6 | 4-methoxyphenyl | 2,6-dimethyl-4-pyridyl | H | H | H | H | H | H | — | — | 0 | NT |
| 7 | 4-hydroxyphenyl | 4-pyridyl | H | H | H | H | H | H | — | — | 0 | 30 |
| 8 | 4-ethoxyphenyl | 4-pyridyl | H | H | H | H | H | H | — | — | 0 | 13 |
| 9 | 4-n-propoxyphenyl | 4-pyridyl | H | H | H | H | H | H | — | — | 0 | 8 |
| 10 | 4-isopropoxyphenyl | 4-pyridyl | H | H | H | H | H | H | — | — | 0 | 26 |

[a]IC$_{50}$ determined on total HETE and Di-HETE production by RBL-1 high speed supernatant.
NT — Not tested.

TABLE IIIA

Consumption of Oxygen by 5-LC Enzyme

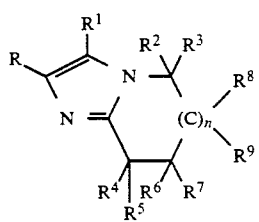

FORMULA (I)

| Compound Number | R | R¹ | R² | R³ | R⁴ | R⁵ | R⁶ | R⁷ | R⁸ | R⁹ | n | 5-LO[a,b] IC$_{50}$ (uM) |
|---|---|---|---|---|---|---|---|---|---|---|---|---|
| 1 | 4-acetylthiophenyl | 4-pyridyl | H | H | H | H | H | H | — | — | 0 | 25 |
| 2 | 4-trimethylacetylthiophenyl | 4-pyridyl | H | H | H | H | H | H | — | — | 0 | 6 |
| 3 | 4-acetoxymethylthiophenyl | 4-pyridyl | H | H | H | H | H | H | — | — | 0 | 47 |
| 4 | 4-ethylthiophenyl | 4-pyridyl | H | H | H | H | H | H | — | — | 0 | 30 |
| 5 | 4-ethylsulfinylphenyl | 4-pyridyl | H | H | H | H | H | H | — | — | 0 | >100 |
| 6 | 4-carbethoxymethylthio | 4-pyridyl | H | H | H | H | H | H | — | — | 0 | 50 |

[a]IC$_{50}$ determined on consumption of oxygen by 5-LO enzyme by RBL-1 high speed supernatant.
[b]NT — Not tested.

TABLE IV

The Effect of Compounds of Formula (I) on 5-Lipoxygenase Activity (LTC$_4$ Production)

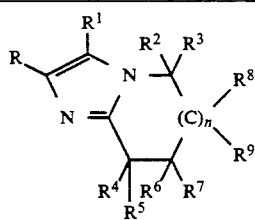

FORMULA (I)

| Compound Number | R | R¹ | R² | R³ | R⁴ | R⁵ | R⁶ | R⁷ | R⁸ | R⁹ | n | 5-LO[a,b] IC$_{50}$ (uM) |
|---|---|---|---|---|---|---|---|---|---|---|---|---|
| 1 | 4-methylthiophenyl | 4-pyridyl | H | H | H | H | H | H | — | — | 0 | 7 |
| 2 | 4-methylsulfinylphenyl | 4-pyridyl | H | H | H | H | H | H | — | — | 0 | 95 |
| 3 | 4-methylsulfonylphenyl | 4-pyridyl | H | H | H | H | H | H | — | — | 0 | 37 |
| 4 | 4-methoxyphenyl | 2-pyridyl | H | H | H | H | H | H | — | — | 0 | 26 |
| 5 | 4-methoxyphenyl | 3-pyridyl | H | H | H | H | H | H | — | — | 0 | 21 |
| 6 | 4-methoxyphenyl | 2,6-dimethyl-4-pyridyl | H | H | H | H | H | H | — | — | 0 | NT |
| 7 | 4-hydroxyphenyl | 4-pyridyl | H | H | H | H | H | H | — | — | 0 | 27 |
| 8 | 4-ethoxyphenyl | 4-pyridyl | H | H | H | H | H | H | — | — | 0 | 12 |

TABLE IV-continued

The Effect of Compounds of Formula (I) on 5-Lipoxygenase Activity (LTC$_4$ Production)

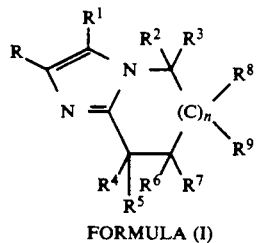

FORMULA (I)

| Compound Number | R | R$^1$ | R$^2$ | R$^3$ | R$^4$ | R$^5$ | R$^6$ | R$^7$ | R$^8$ | R$^9$ | n | 5-LO$^{a,b}$ IC$_{50}$ (uM) |
|---|---|---|---|---|---|---|---|---|---|---|---|---|
| 9 | 4-n-propoxyphenyl | 4-pyridyl | H | H | H | H | H | H | — | — | 0 | 13 |
| 10 | 4-isopropoxyphenyl | 4-pyridyl | H | H | H | H | H | H | — | — | 0 | 13 |
| 11 | 4-acetylthiophenyl | 4-pyridyl | H | H | H | H | H | H | — | — | 0 | 3 |
| 12 | 4-trimethylacetylthiophenyl | 4-pyridyl | H | H | H | H | H | H | — | — | 0 | 4 |
| 13 | 4-acetoxymethylthiophenyl | 4-pyridyl | H | H | H | H | H | H | — | — | 0 | 2.6 |
| 14 | 4-ethylthiophenyl | 4-pyridyl | H | H | H | H | H | H | — | — | 0 | 9 |
| 15 | 4-ethylsulfinylphenyl | 4-pyridyl | H | H | H | H | H | H | — | — | 0 | — |
| 16 | 4-carbethoxymethylthiophenyl | 4-pyridyl | H | H | H | H | H | H | — | — | 0 | 4 |

$^a$IC$_{50}$ determined on LTC$_4$ production by human monocytes.
$^b$NT = not tested

TABLE V

The Effect of Compounds of Formula (I) Eicosanoid Production

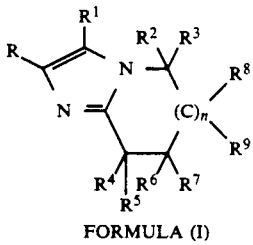

FORMULA (I)

| Compound Number | R | R$^1$ | R$^2$ R$^3$ R$^4$ R$^5$ R$^6$ R$^7$ R$^8$ R$^9$ n | 5-LO, IC$_{50}$ (uM)$^{a,b}$ | | | | | |
|---|---|---|---|---|---|---|---|---|---|
| | | | | tLTB$_4$ | LTB$_4$ | 5-HETE | 12-HETE | 20-OH—LTB$_4$ | TXB$_2$ |
| 1 | 4-methyl-thiophenyl | 4-pyridyl | H H H H H H — — 0 | 30 | 30 | 30 | 60 | 30 | NT |
| 2 | 4-methyl-sulfinylphenyl | 4-pyridyl | H H H H H H — — 0 | 80 | 80 | 80 | 80 | NT | 80 |

$^a$IC$_{50}$ determined on human blood stimulated with calcium ionophore.
$^b$NT = Not Tested

TABLE VI

| | 5-LO Inhibition relative to Compound C | Adverse CNS activity* (Log D) (Lipophilicity) | P-450 Inhibition IC$_{50}$-uM | AAEE (MOUSE ED$_{50}$ mg/kg (po) |
|---|---|---|---|---|
| A. 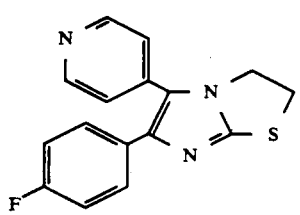 | 1.5 | +++ (2.19) | 0.6 | 27 |

TABLE VI-continued

| | 5-LO Inhibition relative to Compound C | Adverse CNS activity* (Log D) (Lipophilicity) | P-450 Inhibition IC$_{50}$-uM | AAEE (MOUSE ED$_{50}$ mg/kg (po) |
|---|---|---|---|---|
| B. | 0.8 | — (1.20) | 5.0 | 14 |
| C. | 1 | +++ (2.14) | 21.4 | 28 |
| D. | 4 | + (2.68) | 43.7 | 20 |
| E. | NA** | — (0.85) | 866 | 44 |

*Plus sign indicates presence and minus sign absence.
**Not active.

TABLE VII

CNS Toxicity in Mice

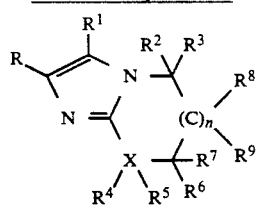

| No. | n | X | R$^1$ | R | Dose mg/kg po | One* Hour | 24* Hours |
|---|---|---|---|---|---|---|---|
| 1** | 0 | SO | 4-pyridyl | 4-methoxyphenyl | 200 | — | — |
| 2 | 0 | S | 4-pyridyl | 4-fluorophenyl | 200 | — | — |
| 3 | 0 | C | 4-pyridyl | 4-fluorophenyl | 200 | + | + |
| 4 | 0 | C | 4-pyridyl | 4-methoxyphenyl | 150 | + | + |
| 5 | 1 | C | 4-pyridyl | 4-methoxyphenyl | 200 | + | + |
| 6 | 0 | C | 4-pyridyl | 4-(1-ethoxy)phenyl | 200 | + | + |
| 7 | 0 | C | 4-pyridyl | 4-methylthiophenyl | 200 | + | + |
| 8 | 0 | C | 4-pyridyl | 4-methylsulfinylphenyl | 200 | — | — |
| 9 | 0 | C | 4-pyridyl | 4-methylsulfonylphenyl | 200 | — | — |
| 10 | 0 | C | 4-pyridyl | 4-ethylthiophenyl | 200 | — | — |
| 11 | 0 | C | 4-pyridyl | 4-ethylsulfinylphenyl | 300 | — | — |
| 12 | 0 | C | 4-pyridyl | 4-acetoxymethylthiophenyl | 200 | — | — |
| 13 | 0 | C | H | 4-pyridyl | 200 | — | — |
| 14 | 0 | C | 4-methylthiophenyl | 4-pyridyl | 200 | + | + |

TABLE VII-continued

CNS Toxicity in Mice

| No. | n | X | $R^1$ | R | Dose mg/kg po | One* Hour | 24* Hours |
|---|---|---|---|---|---|---|---|
| 15 | 0 | C | 4-methylsulfinylphenyl | 4-pyridyl | 200 | — | — |
| 16 | 0 | C | 4-(2-methyl)pyridyl | 4-methylthiophenyl | 200 | — | — |
| 17 | 0 | C | 4-(2-methyl)pyridyl | 4-methylsulfinylphenyl | 200 | — | — |
| 18 | 0 | C | 4-(2-methyl)pyridyl | 4-methoxyphenyl | 200 | — | + |

*Minus sign indicates absence and plus sign presence of convulsions at one hour and death at 24 hours.
**This compound metabolizes to the corresponding sulfide which causes convulsions
$R^2$, $R^3$, $R^4$, $R^5$, $R^6$, $R^7$, $R^8$ and $R^9$ each is hydrogen for compounds numbered to 18 above.

TABLE VIII

P-450 Inhibition

| No. | X | $R^1$ | R | $IC_{50}$ $\mu M$ |
|---|---|---|---|---|
| 1 | S | 4-pyridyl | 4-methoxyphenyl | 12.5 |
| 2 | SO | 4-pyridyl | 4-methoxyphenyl | >100* |
| 3 | $SO_2$ | 4-pyridyl | 4-methoxyphenyl | 26.2 |
| 4 | S | 4-pyridyl | 4-fluorophenyl | 0.9 |
| 5 | C | 4-pyridyl | 4-methoxyphenyl | 21.4 |
| 6 | S | 4-fluorophenyl | 4-pyridyl | 0.5 |
| 7 | C | 4-pyridyl | 4-(1-ethoxy)phenyl | 8.4 |
| 8 | C | 4-pyridyl | 4-(1-propoxy)phenyl | 62.7 |
| 9 | C | 4-pyridyl | 4-(2-propoxy)phenyl | 2.5 |
| 10 | C | 4-N-methyl-pyridyl | 4-methoxyphenyl | 108 |
| 11 | C | 4-pyridyl | 4-methylthiophenyl | 43.7 |
| 12 | C | 4-pyridyl | 4-methylsulfinylphenyl | 866 |
| 13 | C | 4-pyridyl | 4-methylsulfonylphenyl | >100 |
| 14 | C | 4-pyridyl | 4-ethylthiophenyl | 28.1 |
| 15 | C | 4-pyridyl | 4-ethylsulfinylphenyl | >100 |
| 16 | C | 2-pyridyl | 4-methoxyphenyl | >100 |
| 17 | C | 3-pyridyl | 4-methoxyphenyl | >100 |
| 18 | C | H | 4-pyridyl | 80.1 |
| 19 | C | 4-methylthio-phenyl | 4-pyridyl | 5.2 |
| 20 | C | 4-methylsulfinyl-phenyl | 4-pyridyl | 13.7 |
| 21 | C | 4-(2-methyl)-pyridyl | 4-methylthiophenyl | 57.5 |
| 22 | C | 4-(2-methyl)-pyridyl | 4-methylsulfinylphenyl | >1000 |
| 23 | C | 4-(2-methyl)-pyridyl | 4-methoxyphenyl | 56.6 |

$R^2$, $R^3$, $R^4$, $R^5$, $R^6$, $R^7$, $R^8$, and $R^9$ each is hydrogen and n is 0 for compounds numbered 1 to 23 above.

It has now been found that the compounds of the present invention have superior properties over previously known compounds as summarized by the data in Table VI. Compound A, 5-(4-pyridyl)-6-(4 fluorophenyl)-2,3-dihydroimidazo[2,1-b]thiazole, and compound B, 5-(4-pyridyl)-6-(4-fluorophenyl)-2,3-dihydroimidazo [2,1-b]thiazole oxide, are representative of compounds taught in U.S. Pat. No. 4,175,127 issued Nov. 20, 1979. Compound C,2-(4-methoxyphenyl)-3-(4-pyridyl)-6,7-dihydro-[5H]-pyrrolo[1,2-a]imidazole is specifically taught in U.S. Pat. No. 4,719,218 issuing from the parent case of the present application. Compound D, 2-(4-methylthiophenyl)-3-(4-pyridyl)-6,7-dihydro-[5H]-pyrrolo[1,2-a]imidazole and compound E, 2-(4-methylsulfinylphenyl)-3-(4-pyridyl)-6,7-dihydro-[5H]-pyrrolo[1,2-a]imidazole are representative of the present invention.

Structural modifications described in this application have reduced the severity, when compared to prior art compounds, of two undesirable side effects: 1) CNS toxicity; and 2) inhibition of cytochrome P-450 dependent enzyme activities, which is a deficiency that could result in clinically relevant drug interactions. More specifically, the elimination of the sulfur on the bicyclic fused ring nucleus of the compounds and replacement of the fluorine with a methoxy group reduced inhibition of cytochrome P-450 dependent enzymes, but did not eliminate the presence of adverse central nervous system (CNS) activity. This is shown by a comparison of the data in Table VI for compound C with A. It was believed that the CNS effects were related to the ability of a compound to penetrate the CNS and hence to lipophilicity. Compounds A and C are both highly lipophilic and demonstrated similar CNS effects. The log D shown on Table VI is a measure of lipophilicity determined via high pressure liquid chromatography. However, it was found that introduction of polarity into the phenyl ring, pyridyl ring, or bicyclic fused ring reduced 5-lipoxygenase inhibition activity. A comparison of compounds D and E in Table VI demonstrate this effect for introduction of polarity into the phenyl ring and comparison of compounds A and B demonstrates this effect for the bicyclic fused ring.

A comparison of compounds A and B demonstrated a reduction in the undesirable CNS activity. A similar effect is shown comparing claimed compounds D and E. Incorporation of polarity into A yielded compound B, and reduced CNS toxicity. Incorporation of polarity into compound D yielded compound E, and reduced CNS toxicity. Further compound E is metabolized in vivo to compound D. Therefore, conversion of a polar but inactive prodrug (E) in vivo to its metabolite (D) reduces CNS toxicity. In addition compound D has less CNS toxicity than prior art compound A. Thus the claimed compounds D and E have reduced inhibition of cytochrome P-450 dependent enzymes and reduced adverse CNS activity. This conclusion is further supported by the following data.

LOG D DETERMINATION

The procedure used to determine the log D's listed on Table VI was as follows. A 20 μl sample was injected into a Shandon Hypersil ODS, 5 μ (100 mm ×4.6 mm ID) column and was eluted using a mobile phase of 65:35 MeOH:H$_2$O (The aqueous portion was 0.01 M in KH$_2$PO$_4$ and adjusted to pH 7.4 with KOH after mixing the MeOH), at a flow rate of 2 ml per minute. Eluting peaks were detected by UV absorbance at 222 nm. All samples were made up at 0.1 mg/ml. (Retentions were identical at 0.01 mg/ml.)

The data was analyzed by determining the regression line corresponding to the logg k' vs. literature log P of the reference standards. (See Unger, S. H. et al., *J. Pharm. Sci.*, 67, 1364 (1978). The log P (log D) was then determined for the test sample from its log k' on this line. Reproduciblity was usually better than 0.5%.

The reference standards and their literature log P's included NaNO$_2$, 0.0; acetanalide, 1.16; acetophenone, 1.66; anisole, 2.08; chlorobenzene, 2.84; benzophenone, 3.18; anthracene, 4.45; and pentachlorobenzene, 5.12.

CNS ACTIVITY

Effects on the central nervous system (CNS) of the claimed and prior art compounds was demonstrated in cynomolgus monkeys.

Oral administration of 90 mg/kg/day of compound A on Table VI, 5-(4-pyridyl)-6-(4-fluorophenyl)-2,3-dihydro imidazo[2,1-b]thiazole to two cynomolgus monkeys (1 female, 1 male) for two consecutive days induced body tremors in both monkeys and severe, recurrent convulsions in the male animal. Administration of 30 mg/kg/day of compound A on Table VI to two cynomolgus monkeys (1 female, 1 male) for 5 or 6 consecutive days was associated with emesis and gastric ulceration in both monkeys but with no evidence of convulsions or body tremors. Monkeys, when administered a second dose of 90 mg/kg of compound A died with convulsions within 1 to 5 hours after dosing.

A single oral dose of 90 mg/kg of compound C in Table VI, 2-(4-methoxyphenyl)-3-(4-pyridyl)-6,7-dihydro[5H]-pyrrolo[1,2-a]imidazole to 1 female and 1 male monkey resulted in death of both animals. The male became sedated, lost consciousness and died within 1.5 hours of dosing; the female demonstrated both decreased motor activity and convulsions prior to death within 3.5 hours of dosing. A single oral dose of 60 mg/kg to two additional monkeys resulted in sedation, loss of consciousness and death of one (male) within 1 hour of dosing. Additional monkeys tolerated repeated doses of 45 mg/kg or 30 mg/kg and one animal tolerated an escalating dose schedule of 30-90-120 mg/kg.

Two monkeys (1 female, 1 male) were gavaged with 90 mg/kg of compound E, 2-(4-methylsulfinylphenyl)-3-(4-pyridyl)-6,7-dihydro-[5H]-pyrrolo[1,2-a]imidazole, and clinical effects were not observed. Additional monkeys were orally administered 200, 400 or 800 mg/kg of compound E to probe the limiting dose and toxic effect(s). Both monkeys receiving 800 mg/kg died, the female within 2 hours of dosing and the male between 12-24 hours of dosing. Convulsions in these animals were not observed.

The two monkeys administered 400 mg/kg were repeatedly administered this dose for 7 consecutive days; each animal experienced emesis within 1 to 5 hours of dosing after the 1st, 3rd and 4th doses, whereas only the female experienced emesis after the 5th, 6th and 7th doses. A complete necropsy, serum clinical chemistry, hematology and histological examination was completed on both monkeys. Evidence of drug related change was not observed. Emesis was the only observation in monkeys administered 400 mg/kg/day of compound E for 7 consecutive days.

In summary, compounds A and C each caused convulsions and death after either two or one doses respectively of 90 mg/kg, while compound E at that dosage caused no observable clinical effects. Compound E administered at 400 mg/kg/day for seven days caused only emesis. Thus compound E does not have the adverse CNS effects demonstrated by the prior art compounds A and C.

Effects on the central nervous system of the claimed and prior art compounds was also demonstrated in mice as shown by the data in Table VII. For compounds 1 to 5, representative of previously known compounds, convulsions occurred in mice at one hour and death at 4 hours after administration of 3 of 5 compounds. For compounds 6 to 18 representing the present invention, convulsions occurred at one hour upon administration of only 3 of 13 compounds and death occurred at 24 hours for 4 of 13 compounds. This data indicates a general improvement in reducing CNS activity for compounds of the present invention.

CYTOCHROME P-450 INHIBITION

The inhibitory effect of several compounds on hepatic cytochrome P-450 dependent mixed function oxidase activity was evaluated in vitro in rat microsomes using the prototypical substrate, ethoxycoumarin, as follows. Animals: Male Sprague-Dawley rats, 9-10 weeks of age and weighing 300-340 g, were dosed daily with Na-phenobarbital for three days, i.p. (1 ml/kg in ultrapure H$_2$O), at 80 mg/kg/day. The animals were killed by cervical dislocation 24 hours after the last dose and pooled hepatic microsomes were prepared by differential centrifugation. Microsomes were stored at −80° C. In vitro enzyme studies: The possible inhibitory effects of several compounds listed on Table VIII on hepatic cytochrome P-450 dependent mixed function oxidase activity were assessed using ethoxycoumarin-O-deethylase (ECOD) activity. The deethylation of the substrate, 7-ethoxycoumarin, is detected by measuring the fluorescence of 7-hydroxycoumarin according to the method of Lee N. H. et al., *Toxicologist*, 5, 164 (1985). Microsomal incubations consisting of 15 μl pooled Na-phenobarbital induced microsomes (approx. 0.3 mg/ml microsomal protein) and 875 μl reaction mixture of 0.45 mM 7-ethoxycoumarin, 5 mM glucose-6-phosphate, 0.5 units/ml glucose-6-phosphate dehydrogenase and 5 mM MgCl$_2$ in 0.1 M N-2-hydroxyethylpiperazine N'-2-ethanesulfonic acid,, pH 7.8 were prepared. Varying concentrations of the test compounds, dissolved in a small amount of dimethyl sulfoxide (10 μl), were added directly to the incubations. Solvent controls were incubated in the presence of dimethyl sulfoxide. After a two minute preincubation at 37° C., the deethylation reaction was initiated by adding 100 μl 0.74 mM B-nicotinamide adenine dinucleotide phosphate/0.74 mM B-nicotinamide adenine dinucleotide. The reaction was stopped after incubating for 10 minutes at 37° C. by adding 2.5 ml basic MeOH, pH 9.0. The samples were spun at 2500 revolutions per minute for 15 minutes. Two mls of the supernatent was transferred into disposable fluorescence cuvets and the fluorescence of each sample was measured at the excitation wavelength 390 nm and emission wavelength 454 nm. The PROBIT procedure was used to calculate $IC_{50}$ values according to the SAS Institute Inc., SAS User's guide: Statistics, 1982 Edition, Cary NC: SAS Institute Inc. 1982, 287 pp.

The results are summarized in Table VIII and demonstrate that compounds of the claimed invention have reduced inhibition of P-450 enzyme compared to previously known compounds. Compounds 1 to 6 represent previously known compounds. The $IC_{50}$, which is the concentration at which 50% of the enzyme activity is inhibited, was less than 30 μM for each of these compounds except compound 2. Compounds 7 to 23 represent the claimed invention. The majority of these compounds have an $IC_{50}$ above 30 μM. Compounds of the claimed invention, because of the reduced inhibition of cytochrome P-450 dependent enzymes, would be expected to have significantly less clinically relevant drug interactions than prior art compounds.

The following examples are to be construed as merely illustrative and not a limitation of the scope of the present invention in any way.

Temperature is in degrees Centigrade (°C).

EXAMPLE 1

2-(4-Fluorophenyl)-6,7-dihydro-(5H)-pyrrolo[1,2-a]imidazole (Formula (E) Compound)

Method A

A stirred solution of 15 g (87 mmoles) of 2-chloro-4-fluoroacetophenone in 75 ml of SD 30 alcohol was treated at 25° C. with 10.65 g (104 mmoles) of 2-iminopyrrolidine, resulting in an exothermic temperature rise to 40° C. After stirring for one hour (hr), approximately 75 ml of ethyl acetate was added, and the mixture was extracted with dilute HCl to dissolve the precipitate. The aqueous acidic extract was separated from the organic phase, adjusted to a pH between 4 and 5, and heated on a steam bath for 24 hrs. The solution was adjusted to pH 2, extracted with ether, brought to pH 8, and extracted with methylene chloride. The basic organic phase was chromatographed on silica, eluting with 4% methanol in methylene chloride. The residue obtained on concentration of the pooled fractions was recrystallized from CCl4, melting point (mp) 137.5°–139° C.

Method B (a)

1-(4-Fluorophenyl)-2-(2-iminopyrrolidin-1-yl)-ethanone hydrocholoride (Formula (H) compound A stirred solution of 37.3 g (216 mmoles) of 2-chloro-1-(4-fluorophenyl)-ethanone (prepared as described by Joshi et al., *J. Heterocyclic Chem.* 16, 1141 (1979)) in 70 ml of chloroform chilled in a methanol-ice bath between 15°–18° C., was treated with a solution of 20 g (238 mmoles) of 2-imino-pyrrolidine in 50 ml of chloroform at such a rate as to maintain the temperature of the reaction mixture. After an additional 2 hours, the mixture was triturated with 300 ml Et₂O, filtered, and the crystals were washed with ether and recrystallized from alcohol to give white needles of the named Formula (H) compound, mp 207°–208° C.

Anal. Calcd. for $C_{12}H_{14}Cl\ F\ N_2O$: C, 56.15; H, 5.50; N, 10.91. Found: C, 56.14; H, 5.50; N, 10.90.

(b) 2-(4-Fluorophenyl)-6,7-dihydro-(5H)-pyrrolo[1,2-a]imidazole (Formula (E) Compound)

An aqueous solution of 31 g (0.12 mole) of the named Formula (H) compound of Method B, part a above, was heated in 300 ml of water on a steam bath for 8 hours. The solution was adjusted to pH 6.5, and the resulting precipitate was filtered, dried under vacuum and recrystallized from CCl4 to give the named Formula (E) compound, mp 137.5°–139° C.

Anal. Calcd. for $C_{12}H_{11}FN_2$: C, 71.27; H, 5.48; N, 13.85. Found: C, 71.00; H, 5.61; N, 13.73.

EXAMPLE 2

2-(4-Fluorophenyl)-3-(4-pyridyl)-6,7-dihydro-[5H]-pyrrolo[1,2-a]imidazole

A stirred solution of 13.1 g (0.065 mole) of 2-(4-fluorophenyl)-6,7-dihydro-[5H]-pyrrolo[1,2-a]imidazole, prepared as described in Example 1, and 51.4 g (0.65 mole) of dry pyridine in 17 ml of dry methylene chloride at 22°–25° C. was treated over 1.5 hours (hr) with 35.3 g (0.325 mmole) of ethyl chloroformate. The solution was stirred at 25° C. overnight, and the treatment with pyridine and ethyl chloroformate repeated as before, followed by a 24 hr period of stirring. After 3 more treatments as described above, the solvent was removed in vacuo. The residue was dissolved in 5% aqueous NaHCO₃ and extracted into methylene chloride. The organic phase was washed with 5% aqueous NaHCO₃ and dried over anhydrous K₂CO₃. The volatile solvents were removed in vacuo and the residue extracted into methylene chloride. The organic phase was extracted repeatedly with 0.2 M HCl until traces of starting material were removed, then washed with 5% Na₂CO₃ solution, dried over K₂CO₃ (anhydrous), and striped in vacuo. The residue was crystallized from toluene hexane to give the compound of Formula (F) known as 3-(N-ethoxycarbonyl-1,4-dihydro-4-pyridyl)-2-(4-fluorophenyl)-6, m.p. 146°–147° C.

Method A 0.5 g (1.4 mmoles) of the Formula (F) product described in Example 2 was heated with stirring in 5ml of decalin under argon. Upon reaching a temperature of 80° C., 0.06 g (1.8 mmoles) of sulfur was added and the mixture heated to 165° C. until starting material was consumed. The cooled mixture was filtered and the solid washed with petroleum ether and dissolved in chloroform ethyl acetate (1:1). This solution was decolorized with Darco, and chromatographed on silica. Elution with 20% methanol in chloroform ethyl acetate (1:1) afforded a fraction which was concentrated in vacuo, and recrystallized from carbon tetrachloride to give the desired Example II title product, mp 163°–164.5° C.

Method B 15.0 g (42.4 mmoles) of a Formula (F) compound, i.e., 3-(N-ethoxycarbonyl-1,4-dihydro-4-pyridyl)-2-(4-fluorophenyl)-6,7-dihydro[5H]-pyrrolo[1,2-a]imidazole, prepared as described above, was added to a stirred solution of 28.6 g (255 mmoles) of potassium tert.-butoxide dissolved in tert.-butanol (250 ml) into which O₂ was being bubbled. The solution was heated to reflux for 15 minutes, and the solvent then removed in vacuo. The solid product was extracted into methylene chloride, washed with water and then extracted into aqueous 3N HCl. This aqueous acidic phase was made basic with cold 10% aqueous sodium hydroxide and extracted with methylene chloride. The resulting organic phase was dried over anhydrous $K_2CO_3$ and the solvent was removed in vacuo. Two recrystallizations from toluene gave the Example II title product, mp 165°–166° C. Anal. Calcd. for $C_{17}H_{14}FN_3$:C, 73.10; H, 5.05; N, 15.04. Found: C, 73.31; H, 5.11; N, 15.08.

EXAMPLE 3

2-(4-Methylthiophenyl)-3-(4-pyridyl)-6,7-dihydro-[5H]-pyrrolo[1,2-a]imidazole

A stirred solution of 5.5 g (19.7 mmoles) of 2-(4-fluorophenyl)-3-(4-pyridyl)6,7-dihydro-[5H]-pyrrolo[1,2]imidazole, prepared as described in Example 2 in 75 ml of dry (sieve) dimethylformamide was treated with 1.65 g (23.6 mmoles) of sodium thiomethylate under argon atmosphere. The reaction mixture was heated overnight at 75° C. followed by an additional 2 hours at 95° C., poured into cold water and extracted twice with ethyl acetate. The organic phase was washed three times with water, dried over anhydrous potassium carbonate, and stripped in vacuo. The residue was recrystallized twice from ethyl acetate to afford the titled compound, mp 171°–172° C.

Anal. Calcd. for $C_{18}H_{17}N_3S$: C, 70.33; H, 5.57; N, 13.67; S, 10.43. Found: C, 69.93; H, 5.40; N, 13.76; S, 10.75.

EXAMPLE 4

2-(4-Methylsulfinylphenyl)-3-(4-pyridyl)-6,7-dihydro-[5H]-pyrrolo[1,2-a]imidazole To a stirred solution of 5.0 g (16.3 mmoles) of (4-methylthiophenyl)-3-(4-pyridyl)-6,7-dihydro-[5H]-pyrrolo[1,2-a]imidazole of Example 3 dissolved in 75 ml of chloroform, chilled in an ice bath, was added dropwise a solution of 3.30 g (16.3 mmoles) of 85% 3-chloroperbenzoic acid in chloroform. After stirring at 25° C. overnight, the reaction mixture was washed with 5% sodium carbonate, dried over anhydrous potassium carbonate, and stripped in vacuo. The residue was flash chromatographed on silica eluting with 5 to 10% methanol in methylene chloride: 2-propanol (9:1). The solvent was removed in vacuo and the residue recrystallized from ethyl acetate to give the desired titled compound, mp 163.5°–165.5° C. $^1$H NMR (360 MHz, CDCl$_3$) δ 8.62 (2H,d), 7.68 (2H,d), 7.57 (2H,d), 7.25 (2H,d), 4.05 (2H,t), 3.02 (2H,t), 2.72 (s) superimposed upon 2.69 (m) (5H total). Mass Spec.

(Cl)

(M+H) 324 (MW=323).

EXAMPLE 5

2-(4-Methylsulfonylphenyl)-3-(4-pyridyl)-6.7-dihydro-[5H]-pyrrolo[1,2-a]imidazole A stirred solution of 0.64 g (1.98 mmoles) of 2-(4-methylsulfinylphenyl)-3-(4-pyridyl)-6,7-dihydro-[5H]pyrrolo[1,2-a]imidazole of Example 4 in water was treated dropwise over 45 minutes with an aqueous solution of 0.209 g (1.32 mmoles) of potassium permanganate. After stirring overnight, the suspension was extracted with methylene chloride. The organic phase was dried over anhydrous potassium carbonate and stripped in vacuo. The residue flash chromatographed in silica eluting with 2 to 4% methanol in chloroform. The solvent was removed in vacuo and the residue recrystallized from ethyl acetate to afford the desired titled compound, mp 222.5°–224° C. $^1$H NMR (250 MHz, CDCl$_3$) δ 8.62 (2H,d), 7.85 (2H,d), 7.72 (2H,d), 7.26 (2H,d), 4.05 (2H,t), 3.05(s) superimposed upon 3.03(t) (5H total), 2.70 (2H,q).

EXAMPLE 6

2-(4-Methoxyphenyl)-6,7-dihydro-[5H]-pyrrolo-[1,2-a]imidazol-3-yl-tri-n-butyltin a)

2-(4-Methoxyphenyl)-6,7-dihydro-[5H]-pyrrolo[1,2-a]imidazole (Formula (E) Compound)

To a solution of 6.8 g (29.7 mmoles) of 2-bromo-4'-methoxyacetophenone in 50 ml of CHCl$_3$ was added a solution of 5 g (59.4 mmoles) of 2-iminopyrrolidine in 30 ml of CHCl$_3$ with chilling. After 4 hours of stirring at 25° C., the solvent was removed in vacuo. The residue was dissolved in water, the pH adjusted to 2.5 and the solution heated on a steam bath under argon atmosphere for 8 hours. The cooled solution was adjusted to pH 6. The resulting precipitate was filtered, washed with water and dried in vacuo to afford the titled compound, mp 116°–117.5° C.

b)

2-(4-Methoxyphenyl)-6,7-dihydro-[5H]-pyrrolo[1,2-a]imidazol-3-yl-tri-n-butyltin

To an ice cold (0° C.) solution of [16.8 g, 0.078 mol] 2-(4-methoxyphenyl)-6,7-dihydro-[5H]-pyrrolo[1,2-a]imidazole in 200 ml of dry tetrahydrofuran under argon was added dropwise over 20 minutes 35 mL [0.0858 mol] of a 2.5M solution of n-butyl lithium in hexane. Once the addition was complete, the deep-red solution was stirred in the cold for five minutes and then a solution of the tributyltin chloride [26.4 g, 0.0975 mol] in 50 ml of dry tetrahydrofuran was added over 20 min. The reaction mixture was stirred at ice-bath temperatures for 1.5 hours and then saturated ammonium chloride was added. The layers were shaken together and separated and the organic extract was washed an additional time with saturated ammonium chloride and then dried with anhydrous potassium carbonate. The solvent was removed in vacuo to give 50 g of a crude oil, which was taken up twice in cold hexane, filtering off the unreacted 2-(4-methoxyphenyl)-6,7-dihydro-[5H]-pyrrolo[1,2-a]imidazole each time. The product was purified on a column of silica, eluting with 1:1 ethyl acetate/hexane in the presence of 1% diethylamine, to give 19.2 g (49% of a yellow oil.

Anal. Calcd for $C_{25}H_{40}Sn\ N_2O$: C, 59.66, H, 8.01; N, 5.57. Found: C,59.32; H, 8.01, N,5.41.

EXAMPLE 7

2-(4-Methoxyphenyl)-3-(2-pyridyl)-6,7-dihydro-[5H]-pyrrolo-[1,2-a]imidazole

A solution of 2-bromopyridine (0.948 g, 0.006 mol) in 2 ml of hexamethylphosphoramide and 10 mL of dry tetrahydrofuran was deoxygenated with argon for 30 minutes in the dark. To this solution was added 70 mg of tetrakis (triphenylphosphine)palladium; the reaction was heated to 50° C. for 15 minutes and then it was allowed to return to room temperature. The Formula (J) tin-intermediate prepared as in Example 6 (1 g, 0.002 mol) in 10 ml of dry tetrahydrofuran was then added dropwise. The reaction mixture was heated to reflux for 24 hours and then worked up by adding ethyl acetate and twice shaking the organic extract with 10% potassium fluoride solution, washing with water twice and then drying with saturated sodium chloride solution and anhydrous magnesium sulfate. The organic extract was concentrated in vacuo to give an oil which was purified by flash chromatography in silica, eluting with 20–50% isopropanol in hexane. The resulting solid was recrystallized from ethyl acetate, mp. 142.5°–145° C.;

NMR (CDCl$_3$)δ: 8.55 (d, 1H), 7.45 (d, 2H), 7.4–6.9 (m, 3H), 6.8 (d, 2H), 4.25 (t, 2H), 3.8(s, 3H) 2.9 (t, 2H), 2.6 (m, 2H).

Mass Spec. (CI)(M+H) 292 (MW=291).

EXAMPLE 8

2-(4-Methoxyphenyl)-3-(3-pyridyl)6,7-dihydro-[5H]-pyrrolo[1,2-a]imidazole

The reaction was carried out as described in Example 7 for 2-bromopyridine. Commercially available 3-bromo-pyridine was used in synthesis of the above named compound. The molar amounts were also the same. The crude product was purified by flash chromatography on silica, eluting with 20–30% isopropanol in hexane. The duct was recrystallized from ethyl acetate. mp. 164°–165° C.

NMR (CDCl$_3$)δ: 8.6 (m 2H), 7.65 (m, 1H), 7.45 (d, 2H), 7.3 (m, 1H), 6.8 (d, 2H), 4.0 (t, 2H), 3.8 (s, 3H), 3.0 (t, 2H), 2.65 (m, 2H).

Mass Spec (CI)(M+H)+ =292 (MW=291).

EXAMPLE 9

(4-Methoxyphenyl)-3-(2,6-dimethyl-4-pyridyl)-6,7-dihydro-[5H]-pyrrolo[1,2-a]-imidazole The 4-bromo-2,6-lutidine used in the palladium catalyzed coupling reaction was synthesized from commercially-available 2,6-lutidine N-oxide as described in the literature [J.O.C., 27, 1665 (1962), R. F. Evans and H. C. Brown]. The coupling reaction was carried out as described previously in Example 7.

The product was purified by flash chromatography, on silica, eluting with 20–50% isopropanol in hexane.

NMR(CDCl$_3$)δ: 7.4 (d, 2H), 7.2(s,2H) 6.8 (d, 2H), 4.2 (t, 2H), 3.8 (s, 3H), 2.9 (s, 2H) 2.65 (m, 2H), 2.55 (s, 6H).

EXAMPLE 10

2-(4-Hydroxyphenyl)3-(4-pyridyl)6,7-dihydro-[5H]-pyrrolo[1,2-a]imidazole dihydrobromide a. 2-(4-Methoxyphenyl)-6,7-dihydro-[5H]-pyrrolo[1,2-a]imidazole (Formula (E) Compound)

To a solution of 6.8 g (29.7 mmoles) of 2-bromo-4'-methoxyacetophenone in 50 ml of CHCl$_3$ was added a solution of 5 g (59.4 mmoles) of 2-iminopyrrolidine in 30 ml of CHCl$_3$ with chilling. After 4 hours of stirring at 25° C., the solvent was removed in vacuo. The residue was dissolved in water, the pH adjusted to 2.5 and the solution heated on a steam bath under argon atmosphere for 8 hours. The cooled solution was adjusted to pH 6. The resulting precipitate was filtered, washed with water and dried in vacuo to afford the titled compound, mp 116°–117° C.

b.
3-(N-Ethyloxycarbonyl-1,4-dihydro-4-pyridyl)-2-(4-methoxyphenyl)-6,7-dihydro-[5H]-pyrrolo[1,2-a]imidazole A stirred solution of 2.8 g (13.1 mmoles) of 2-(4-methoxyphenyl)-6,7-dihydro-[5H]-pyrrolo[1,2-a] imidazole, prepared as described above, and 6.2 g (78.4 mmoles) of dry pyridine in 30 ml of dry CH$_2$Cl$_2$ was treated dropwise over 1 hour at 5° C. under argon atmosphere with 4.25 g (30.2 mmoles) of ethyl chloroformate. After stirring for 1 hour an additional 3.1 g (39.2 mmoles) of pyridine was added, followed by 2.15 g (19.8 mmoles) of ethyl chloroformate added over 2 hours. The mixture was stirred overnight at 25° C., then poured into ice water made alkaline with Na$_2$CO$_3$ and extracted with CH$_2$Cl$_2$. The organic phase was sequentially washed with 0.2 N HCl, water, and aqueous K$_2$CO$_3$ solution, dried over Na$_2$SO$_4$ and stripped in vacuo to afford the titled compound as an amber resin.

c.
2-(4-Methoxyphenyl)-3-(4-pyridyl)-6,7-dihydro-[5H]-pyrrolo[1,2-a]imidazole (Formula (I) Compound)

4.1 g (11.2 mmole) of the compound described in Part b) above was heated with stirring in 25 ml of decalin under argon. Upon reaching 85° C., the solid was dissolved, and 0.468 g (14.6 mmoles) of sulfur was added. The mixture was heated to 165° C. and another 0.235 g (7.3 mmoles) of sulfur was added. After another 45 minutes, the starting material was consumed, and the cooled reaction mixture was diluted with 25 ml of petroleum ether and filtered. The filtered solid was washed with additional petroleum ether, dissolved in CHCl$_3$-EtOAc and chromatographed on silica. The material eluting with 8 to 25% methanol in CHCl$_3$-EtOAc (1:1) was concentrated in vacuo and recrystallized from toluene-cyclohexane to give the desired product, mp 157.5°–158.5° C.; Anal. Calcd. for C$_{18}$H$_{17}$N$_3$O:C, 74.20; H, 5.88; N, 14.42. Found: C, 74.09; H, 5.88; N, 14.45.

d.
2-(4-Hydroxyphenyl)-3-(4-pyridyl)-6,7-dihydro-[5H]-pyrrolo[1,2 -a]imidazole dihydrobromide A stirred solution of 3 g (10.3 mmoles) of 2-(4-methoxyphenyl)-3-(4-pyridyl)-6,7-dihydro-[5H]-pyrrolo[1,2-a]imidazole of Part c) above in 150 ml of dry methylene chloride was treated dropwise at −80° C. with a solution of 17.7 g (30.9 mmoles) of boron tribromide in methylene chloride and allowed to warm to room temperature overnight. The reaction mixture was chilled in an ice bath, 5 to 10 ml of water added, and the solvent removed in vacuo. The residue was recrystallized from hot water containing 0.5 ml. of 48% hydrobromic acid and dried in vacuo to afford the titled compound as bright yellow crystals, mp 257°–258° C. Anal. Calcd. for C$_{17}$H$_{15}$N$_3$O.2HBr.½H$_2$O: C, 45.87; H, 4.00; N, 9.44. Found: C,45.66; H, 3.69; N,9.67.

EXAMPLE 11

2-(4-Ethoxyphenyl)-3-(4-pyridyl)6,7-dihydro-[5H]-pyrrolo-[1,2-a]imidazole

A stirred solution of 1.2 g (2.7 mmoles) of 2-(4-hydroxyphenyl)-3-(4-pyridyl)-6,7-dihydro-[5H]-pyrrolo-[1,2-a]imidazole dihydrobromide of Example 10 in 25 ml of dry dimethylformamide cooled in an ice bath was treated with 360 mg (9.0 mmoles) of 60% sodium hydride dispersion and allowed to warm to room temperature. A solution of 420 mg (2.7 mmoles) of ethyl iodide in 2 ml of dimethylformamide was added dropwise, and after 2 hours an additional 105 mg (0.67 mmole) of ethyl iodide was added followed by another 90 mg (2.25 mmoles) of 60% sodium hydride suspension. After stirring overnight, the mixture was poured into 10 volumes of ice water and extracted three times with ethyl acetate. The organic phase was washed with water, dried over anhydrous potassium carbonate and concentrated in vacuo. The residue was flash chromatographed on silica and the fractions eluting with 4 to 6% methanol in chloroform were combined, concentrated in vacuo, and recrystallized from ethyl acetate to afford the titled compound, mp 133°–135° C. Anal. Calcd. for $C_{19}H_{19}N_3O$: C, 74.73, H, 6.27; N, 13.76. Found: C, 74.23; H, 6.01; N, 13.74.

EXAMPLE 12

2-(4-(1-Propoxy)phenyl)-3-(4-pyridyl)-6,7-dihydro-[5H]-pyrrolo[1,2-a]imidazole

A stirred solution of 1.2 g (2.7 mmoles) of 2-(4-hydroxyphenyl) 3-(4-pyridyl)-6,7-dihydro[5H]-pyrrolo-[1,2-a]imidazole dihydrobromide of Example 10 in 20 ml of dry dimethylformamide cooled in an ice bath was treated with 360 mg (9.0 mmoles) of 60% sodium hydride dispersion and allowed to warm to room temperature. 450 mg (2.7 mmoles) of powdered potassium iodide was added, followed by dropwise addition of a solution of 332 mg (2.7 mmoles) of 1-propyl bromide in 2 ml of dimethylformamide. After 2 hours an additional 83 mg (0.67 mmole) of 1-propyl bromide was added followed by another 90 mg (2.25 mmoles) of 60% sodium hydride suspension, and the mixture heated to 65° C. for 2.5 hours. After stirring overnight, the mixture was poured into 10 volumes of ice water and extracted three times with ethyl acetate. The organic phase was washed with water, dried over anhydrous potassium carbonate and concentrated in vacuo. The residue was flash chromatographed on silica and the fractions eluting with 3 to 6% methanol in chloroform were combined, concentrated in vacuo, and recrystallized from ethyl acetate to afford the titled compound, mp 148.5°–150° C. Anal. Calcd. for $C_{20}H_{21}N_3O$: C, 75.21; H, 6.63; N, 13.16. Found: C, 74.95; H, 6.59; N, 13.17.

EXAMPLE 13

2-(4-(2-Propoxy)phenyl)-3-(4-pyridyl)-6,7-dihydro-[5H]-pyrrolo[1,2-a]imidazole

A stirred solution of 0.90 g (2.0 mmoles) of 2-(4-hydroxyphenyl)-3-(4-pyridyl)-6,7-dihydro-[5H]-pyrrolo[1,2-a]imidazole dihydrobromide of Example 10 in 20 ml of dry dimethylformamide cooled in an ice bath was treated with 267 mg (6.67 mmoles) of 60% sodium hydride dispersion and allowed to warm to room temperature. A solution of 374 mg. (2.22 mmoles) of 2-propyl iodide in 2 ml of dimethylformamide was added dropwise and the reaction mixture heated at 100° C. for 4 hours. Another 35 mg (0.88 mmole) of 60% sodium hydride suspension was added at room temperature, followed by 113 mg (0.67 mmole) of 2-propyl iodide and the mixture heated at 100° C. for an additional 3 hours. After stirring overnight, the mixture was poured into 10 volumes of ice water and extracted three times with ethyl acetate. The organic phase was washed with water, dried over anhydrous potassium carbonate and concentrated in vacuo. The residue was flash chromatographed on silica and the fraction eluting with 2% methanol in chloroform, concentrated in vacuo, and recrystallized from ethyl acetate to afford the titled compound, mp 148°–150° C. Anal. Calcd. for $C_{20}H_{21}N_3O$: C, 75.21; H, 6.63; N, 13.16. Found: C, 75.38; H, 6.58; N, 13.26.

EXAMPLE 14

2-(4-Ethylthiophenyl)-3-(4-pyridyl)-6,7-dihydro-[5H]-pyrrolo[1,2-a]imidazole

Sodium hydride (60%) (0.75 g, 19 mmol) was added to a solution of ethanethiol (2.1 ml, 1.7 g, 28 mmol) in N,N-dimethylformamide (15 ml) at 0° C. under an argon atmosphere. After stirring for 0.5 hours, 2-(4-fluorophenyl)-3-(4-pyridyl)-6,7-dihydro-[5H]-pyrrolo[1,2-a]-imidazole (3.5 g, 12.5 mmol) of Example 2 was added and the resulting solution heated to 95° C. for 6 hours. The cooled reaction mixture was evaporated under reduced pressure and the residue partitioned between 1N aqueous sodium hydroxide and dichloromethane. The organic layer was washed successively with water and brine, dried (magnesium sulfate) and concentrated. The residue was chromatographed on silica gel eluting with 25:1 chloroform/methanol. Fractions containing product were combined, the solvent evaporated and the residue recrystallized from ethyl acetate to afford the titled compound; mp. 124°–125° C. Anal. Calcd. for $C_{19}H_{19}N_3S$: C,70 99; H, 5.96; N, 13.08; S, 9.97: Found: C, 70.99; H, 5.92; N, 13.07; S, 9.81.

EXAMPLE 15

2-(4-Ethylsulfinylphenyl)-3-(4-pyridyl)-6,7-dihydro-[5H]-pyrrolo[1,2-a]imidazole The title compound was prepared from 6,7-dihydro 2-(4-ethylthiophenyl)-3-(4-pyridyl)-[5H]-pyrrolo[1,2-a]imidazole of Example 14 by the procedure described in Example 4. mp. 108°–110° . $^1H$ NMR (250 MHz, $CDCL_3$)δ 8.61 (2H, d), 7.65 (2H, d), 7.53 (2H, d), 7.24 (2H, d), 4.05 (2H, t), 3.02 (2H, t), 2.86 (2H, m), 2.69 (2H, m), 1.23 (3H, t).

EXAMPLE 16

2-(4-Mercaptophenyl)-3-(4-pyridyl)-6,7-dihydro-[5H]-pyrrolo-[1,2-a]imidazole

To 5 g (15.5 mmole) of 2-(4-methylsulfinylphenyl)-3-(4-pyridyl)-6,7-dihydro-[5H]-pyrrolo[1,2-a]imidazole prepared as in Example 4 dissolved in 100 ml methylene chloride and cooled to 0° was added 9.7 g (46.4 mmole, 6.5 ml) of trifluoroacetic anhydride in 25 ml of methylene chloride. The mixture was heated to reflux for 1 hour. The reaction mixture was stripped on the rotovap, then treated with water, and extracted with methylene chloride. The extract was washed with 3N $NaHCO_3$ and saturated NaCl and treated with $Na_2SO_4$, then stripped to leave 5.1 g of crude product. This material was dissolved in anhydrous methanol (50 ml) and treated with a 25% solution of $NaOCH_3$/MeOH (5 ml, 23 mmole). This mixture was stirred at room temperature for 3 hours, then poured onto ice water and neutralized with 3N $NaHCO_3$. After removing most of the methanol on the rotovap, the residue was partitioned between methylene chloride and water. The organic layer was washed with water and saturated NaCl, treated with $Na_2SO_4$ and stripped. The residue was flash chromatographed on a silica gel column using a gradient of 1 to 5% MeOH in methylene chloride to give 3.1 g (10.5 mmole) of the titled compound.

EXAMPLE 17

2-(4-Trimethylacetylthiophenyl)-3-(4-pyridyl)-6,7-dihydro-[5H]-pyrrolo[1,2-a]imidazole To 1.0 g (3.4 mmole) of 2-(4-mercaptophenyl)-3-(4-pyridyl)-6,7-dihydro-[5H]-pyrrolo[1,2-a] imidazole prepared as in Example 16 in 50 ml methylene chloride at 0° C. was added a solution of 0.3 g (3.7 mmole, 0.26 ml) trimethylacetyl chloride in 10 ml $CH_2Cl_2$ over a period of 10 minutes. The reaction was allowed to come to room temperature and was stirred for 30 minutes. The mixture was then diluted with methylene chloride and washed with 3N $NaHCO_3$, saturated NaCl, treated with $Na_2SO_4$, stripped, then flash chromatographed on silica with methylene chloride containing 1% to 5% MeOH. The isolated material was recrystallized from ethyl acetate to give 0.43 g of the titled compound. 33.5% yield, mp 216°-217.5° C. $C_{22}H_{23}N_3OS$, Calculated, C: 70.00, H: 6.14, N: 11.13; Found, C: 70.01, H: 6.20, N: 10.99.

EXAMPLE 18

2-(4-Acetylthiophenyl)-3-(4-pyridyl)6,7-dihydro-[5H]-pyrrolo[1,2-a]imidazole

To 1.0 g (3.4 mmole) of 2-(4-mercaptophenyl)-3-(4-pyridyl)-6,7-dihydro-[5H]-pyrrolo[1,2-a]imidazole prepared as in Example 16 in 50 ml methylene chloride at 0° C. was added a solution of 0.3 g (3.7 mmole, 0.26 ml) acetyl chloride in 10 ml $CH_2Cl_2$ over a period of 10 minutes. The reaction was allowed to come to room temperature and was stirred for 30 minutes. The mixture was then diluted with methylene chloride and washed with 3N $NaHCO_3$, saturated NaCl, treated with $Na_2SO_4$, stripped, then flash chromatographed on silica with methylene chloride containing 1% to 5% MeOH. The isolated material was recrystallized twice from ethyl acetate to give 0.20 g of the titled compound. 17.6% yield, mp 152°-154° C. $C_{19}H_{17}N_3OS$, Calculated, C: 68.03, H: 5.11, N: 12.53; Found, C: 68.25, H: 5.40, N: 12.14.

EXAMPLE 19

2-(4-Pyridyl)-6,7-dihydro-[5H]-pyrrolo[1,2-a]imidazole

A stirred suspension of 10 g (35.6 mmoles) of 4-(bromoacetyl)-pyridine hydrobromide and 12.9 g (107 mmoles) of 2-imino-pyrrolidine hydrochloride in 100 ml of dry dimethylformamide was treated with 18.9 g (178 mmoles) of anhydrous sodium carbonate. This suspension was heated at 80° C. overnight in an oil bath. The solvent was removed in vacuo, the residue dissolved in water and extracted with chloroform. The organic layer was washed three times with water, dried over anhydrous potassium carbonate and stripped in vacuo. The residue was chromatographed on silica and eluted with 10-15% methanol in methylene chloride acetone (85:15). This fraction was stripped in vacuo and the solid residue recrystallized twice from ethyl acetate to afford the desired titled compound, mp 140°-141° C., $^1$HNMR (250 MHz, CDCl$_3$) δ 8.62 (2H,d), 7.60(2H,d), 7.34(1H,s), 4.04(2H,t), 2.95 (2H,t), 2.64(2H,q).

EXAMPLE 20

2-[4-(2-Methyl-propenylthio)phenyl]-3-(4-pyridyl)-6,7-dihydro-[5H]-pyrrolo[1,2-a]imidazole.

A solution of 5 g (17 mmoles) of 2-(4-mercaptophenyl)-3-(4-pyridyl)-6,7-dihydro-[5H]-pyrrolo[1,2-a]-imidazole in dry tetrahydrofuran is treated at −20° C. with a solution of 17 mmoles of lithium diethylamide from 6.8 ml of 2.5 M n butyl lithium. After warming, a solution of 1.57 g (17 mmoles) of trimethylsilylmethylchloride in tetrahydrofuran is added dropwise. When the reaction is complete, the mixture is immersed in an ice bath and a second solution (17 mmoles) of lithium diethylamide is added. After stirring for 15 minutes, a solution of 0.99 g (17 mmoles) of acetone in tetrahydrofuran is added, and the mixture is stirred 15 minutes at 0° and 15 minutes at 25° C. The mixture is poured into water, extracted with methylene chloride, and the organic layer dried, and chromatographed on silica to afford the desired titled compound.

EXAMPLE 21

3-(4-Methylsulfinylphenyl)-2-(4-pyridyl)-6,7-dihydro-[5H]-pyrrolo[1,2-a]imidazole a)

2-(4-Pyridyl)-6,7-dihydro-[5H]-pyrrolo[1,2-a]imidazol-3-yl-tri-n-butyltin (Formula (J) Compound)

To a cold (−5° to 0° C.) solution of 0.5 g (2.7 mmol) of 2-(4-pyridyl)-6,7-dihydro-[5H]- pyrrolo[1,2-a]-imidazole prepared as in Example 19, in 20 ml of dry tetrahydrofuran under argon was added 1.08 ml (2.7 mmol) of a 2.5M solution of n-butyllithium in hexane dropwise over 20 minutes. The reaction mixture was stirred for 1.5 hours and then a solution of 1.0 g (3.07 mmol) of tri-n-butyltin chloride in 2 ml of dry tetrahydrofuran was added dropwise. The reaction mixture was then treated with a saturated aqueous solution of ammonium chloride. The organic layer was extracted a second time with saturated ammonium chloride solution and then dried over anhydrous potassium carbonate. The solvent was removed in vacuo and the residue extracted twice with hexane. The extract was concentrated and purified by chromatography on silica eluting with 5-8% methanol in hexane-ethyl acetate (1:1) containing 1% diethyl amine to afford the titled compound as an oil, $^1$HNMR(250 MHz, CDCl$_3$) δ: 8.52 (2H,d), 7.47 (2H,d), 3.97 (2H,t), 2.95 (2H,t), 2.64(2H,g), 1.42 (6H,m), 1.27 (6H,m), 1.08 (6H,m), 0.84(6H,t).

b)

3-(4-Methylthiophenyl)-2-(4-Pyridyl)-6,7-dihydro-[5H]-pyrrolo[1,2-a]imidazole

A solution of 2.69 g (10.9 mmol) of 1-methylthio-4-iodobenzene in 6.8 ml of hexamethyl phosphoramide and 68 ml of dry tetrahydrofuran was purged by bubbling argon through for 15 minutes and then treated with 240 mg of tetrakis(triphenylphosphine)palladium. The mixture was heated at 50° C. for 15 minutes and then treated dropwise with a solution of 1.7 g (3.57 mmol) of compound a) above in 15 ml of dry tetrahydrofuran. The mixture was refluxed in an 80° C. oil bath overnight, then cooled, ethyl acetate added, and washed twice with 10% aqueous sodium fluoride solution, three times with water, and extracted into cold 3N HCL. The aqueous phase was washed twice with methylene chloride, made alkaline with 10% sodium hydroxide, and the product extracted into methylene chloride and dried over anhydrous potassium carbonate. The crude product was purified by flash chromatography on silica eluting with 2-3% methanol in a solution of 66% methylene chloride and 33% acetone containing 2% water. The residue was recrystallized from ethanol ethyl-acetate and dried in vacuo to give the titled compound as yellow crystals, mp 174°–175.5° C.

c) 3-(4-Methylsulfinylphenyl)-2-(4-pyridyl)-6,7-dihydro[5H]-pyrrolo[1,2-a]imidazole A solution of 0.345 g (1.12 mmol) of compound b) above, in 5 ml of water containing 0.75 ml of 3 N hydrochloric acid was treated dropwise at 5° C. over 1.5 hours with a solution of 0.267 g (1.24 mmol) of sodium periodate in 5 ml of water. The reaction mixture was left at this temperature overnight, then warmed to 20° C., extracted twice with methylene chloride, brought to pH 4 and extracted 4 times with methylene chloride, then brought to pH 10 with aqueous sodium carbonate, and extracted into methylene chloride. The organic phase was dried over anhydrous potassium carbonate and concentrated in vacuo. The residue was dissolved in hot ethyl acetate, crystallized and dried in vacuo to give the titled compound, mp 179.5°–181.5° C.

EXAMPLE 22

2-(4-Methylsulfinylphenyl)-3-[4-(2-methyl)pyridyl]-6,7-dihydro-[5H]-pyrrolo[1,2 ]imidazole a) 2-(4-Fluorophenyl)-3-[4-(1-acetyl-2-methyl-1,2-dihydro-pyridyl)]-6,7-dihydro-[5H]-pyrrolo[1,2,a]imidazole To a solution of 3.3 g (11.9 mmole) of 2-(4-fluorophenyl)-3-(4-pyridyl)-6,7-dihydro-[5H]-pyrrolo-[1,2,a]imidazole in dry tetrahydrofuran at −20° C. was added 1.84 g (23.8 mmole) of acetyl chloride. The reaction was stirred at −2° C. for 10 minutes and then 8.81 ml of 2.7M methylmagnesium bromide (20 mmol) was added. The reaction was stirred an additional 15 minutes and then warmed to room temperature for 30 minutes. The reaction was quenched with aqueous NH$_4$Cl, adjusted to pH 7.5 with bicarbonate, and extracted repeatedly with methylene chloride. The combined organic extracts were dried over sodium sulfate, filtered, and concentrated in vacuo to afford the crude dihydropyridine.

b) 2-(4-Fluorophenyl)-3-[4-(2-methyl)pyridyl]-6,7-dihydro-[5H]-pyrrolo[1,2,a]imidazole The crude dihydropyridine was aromatized by heating at 190° C. for 1 hour in a solution composed of 150 ml decalin, 15 ml diglyme, and 1.0 g of sublimed sulfur. The reaction was filtered, diluted with petroleum ether, and chilled. The resulting solid was collected and purified by flash chromatography on silica gel and crystallized from ethyl acetate to afford 2-(4-fluorophenyl)-3-[4-(2-methyl)pyridyl]6,7-dihydro-[5H]-pyrrolo[1,2,-a]imidazole.

c) 2-(4-Methylthiophenyl)-3-[4-(2-methyl)pyridyl]6,7-dihydro-[5H]-pyrrolo[1,2,a]imidazole.

A stirring solution of 0.55 g of compound b) above and 0.16 g of sodium thiomethylate in 7.5 ml of dry dimethylformamide was heated under an argon atmosphere overnight at 120° C. The reaction was poured into cold water and extracted twice with ethyl acetate. The organic phase was filtered, washed three times with water, dried over anhydrous potassium carbonate, and stripped in vacuo. The residue was recrystallized from ethyl acetate to afford the titled compound. NMR 250 MHz (CDCl$_3$)δ: 8.5 (d, 1H), 7.45 (d, 2H), 7.15 (d, 2H), 7.14–7.1 (m, 2H), 4.01 (t, 2H), 3.0 (t, 2H), 2.62 (m, 2H), 2.51 (s, 3H), 2.47 (s, 3H). mp 131°–132° C.

d) 2-(4-Methylsulfinylphenyl)-3-[4-(2-methyl)pyridyl]-6,7-dihydro-[5H]-pyrrolo[1,2,a]imidazole A solution of 200 mg of compound c) above dissolved in 1.5 ml of water containing 1 ml of 1.2 N HCl was treated dropwise at 5° C. over 1.5 hours with a solution of 119 mg of sodium periodate in 1.5 ml of water. The reaction mixture was treated as in Example 21 (c) to yield the titled compound. mp 128°–131° C. NMR 250 MHz (CDCl$_3$)δ: 8.5(d, 1H), 7.7(d, 2H), 7.55(d, 2H), 7.15–7.05(m, 2H), 4.05(t, 2H), 3.05(t, 2H), 2.75(s, 3H), 2.68(m, 2H). In an analogous manner to the process of Example 22(a) and (b), 2-(4-methoxyphenyl) 3-[4-(2-methyl)pyridyl]-6,7-dihydro-[5H]-pyrrolo[1,2-a]imidazole was prepared. mp 158°–160° C.

EXAMPLE 23

2-(4-Carbethoxymethylthiophenyl)-3-(4-pyridyl)-6,7-dihydro-[5H]-pyrrolo[1,2-a]imidazole To 1.0 gm (3.4 mmole) of 2-(4-mercaptophenyl)-3-(4-pyridyl)-6,7-dihydro-[5H]-pyrrolo[1,2-a]imidazole in 50 ml methylene chloride at 0° was added a solution of 0.63 g (3.7 mmole, 0.43 ml) ethyl bromoacetate in 10 ml CH$_2$Cl$_2$ over a period of 10 minutes. The reaction was allowed to come to room temperature and was stirred for 30 minutes. The mixture was then diluted with methylene chloride and washed with 3N NaHCO$_3$, saturated NaCl, treated with Na$_2$SO$_4$, stripped, then flash chromatographed on silica with methylene chloride containing 1% to 5% MeOH. The isolated material was recrystallized from ethyl acetate to give 0.35 g of the titled product. 27.2% yield, mp 102°–103° C. Analyzed for C$_{21}$H$_{21}$N$_3$O$_2$S, Calculated, C: 66.47, H:5.58, N: 11.07; Found, C: 66.39, H: 5.62, N: 10.97.

EXAMPLE 24

2-(4-Acetoxymethylthiophenyl)-3-(4-pyridyl)-6,7-dihydro-[5H]-pyrrolo[1,2-a]imidazole To 1 g (3.1 mmole) of 2-(4-methylsulfinylphenyl)-3-(4 pyridyl)-6,7-dihydro-[5H]-pyrrolo[1,2,a]imidazole was added 25 ml acetic anhydride. The mixture was heated to reflux for 1 hour. The reaction mixture was stripped on the rotovap, then treated with water, and extracted with methylene chloride. The extract was washed with 3N NaHCO$_3$ and saturated NaCl and treated with Na$_2$SO$_4$, then stripped to leave 1.1 g of crude product. This crude material was then flash chromatographed on a silica gel column using a gradient of 1 to 5% MeOH in methylene chloride to give after recrystallization from EtOAc 0.80 g (2.2 mmole) of the titled product. 71% yield, mp 125.5°–126.5° C. Analyzed for C$_{20}$H$_{19}$N$_3$O$_2$S, Calculated, C: 65.73, H:5.24, N: 11 50; Found, C: 66.03, H: 5.26, N: 11.30.

EXAMPLE 25

2-(4-Methylsulfinylphenyl)-3-[4-(2,6-dimethyl)pyridyl]-6,7-dihydro-[5H]-pyrrolo[1,2-a]imidazole a)
2-(4-Fluorophenyl)-6,7-dihydro-[5H]-pyrrolo[1,2-a]imidazole-3-yl-tri-n-butyltin To a −78° C. solution of 2-(4-fluorophenyl)-6,7-dihydro-[5H]-pyrrolo[1,2-a]imidazole (2.0 g, 0.010 mole) in 60 ml of tetrahydrofuran (THF) is added 4.0 ml of 2.5M n-butyllithium. The solution is warmed to −30° C. for 20 minutes and then tributyltin chloride (3.3 g, 0.01 mole) in THF is added. The reaction is allowed to warm gradually to 20° C. and then is quenched with saturated ammonium chloride. Further workup and purification on silica as described in Example 6b yields the titled compound.

b)
2-(4-Fluorophenyl)-3-[4-(2,6-dimethyl)pyridyl]-6,7-dihydro-[5H]-pyrrolo[1,2-a]imidazole The 2-(4-fluorophenyl)-6,7-dihydro-[5H]-pyrrolo[1,2-a]imidazole-3-yl-tri-n-butyltin is coupled with 4-bromo 2,6-lutidine prepared as in Example 9 using the coupling procedure described in Example 7. The product is purified by flash chromatography on silica.

c)
2-(4-Thiomethylphenyl)-3-[4-(2,6-dimethyl)-pyridyl]-6,7-dihydro-[5H]-pyrrolo[1,2-a]imidazole A stirring solution of 2-(4-fluorophenyl)-3-[4-(2,6-dimethyl)pyridyl]-6,7-dihydro-[5H]-pyrrolo[1,2-a]imidazole (0.55g) and sodium thiomethylate (0.16 g) in 7 ml of dry DMF is heated under an argon atmosphere overnight at 120° C. or greater. Then reaction is poured into cold water and extracted twice with ethyl acetate. The combined organic layer is washed with water, dried over potassium carbonate, and stripped in vacuo. Column chromatography on silica yields the titled compound.

d)
2-(4-Methylsulfinylphenyl)-3-[4-(2,6-dimethyl)-pyridyl]-6,7-dihydro-[5H]-pyrrolo[1,2-a]imidazole A solution of the above thiomethyl compound is oxidized using the procedure described in Example 22(d). Column chromatography on silica gives the titled methylsulfinyl compound.

EXAMPLE 26

2(4-Ethoxycarbonylthiophenyl)-3-(4-pyridyl)6,7-dihydro-[5H]-pyrrolo(1,2-a]imidazole To an ice bath cooled solution containing 1.0 g 3.4mmole) of 2-(4-mercaptophenyl)-3-(4-pyridyl)-6,7-dihydro-[5H]-pyrrolo[1,2-a]imidazole prepared as in Example 16 and 0.5 ml (3.6mmole) of triethylamine in 10 ml of methylene chloride is added 0.33 ml (3.5 mmole) of ethyl chloroformate. The reaction is allowed to warm to room temperature and stirred for several hours. Workup and chromatography in a manner analogous to that outlined in Example 18 affords the desired titled compound.

EXAMPLE 27

2-(4-Phenoxythiocarbonylthiophenyl)-3-(4-pyridyl)-6,7-dihydro-[5H]-pyrrolo[1,2-a]imidazole To an ice bath cooled solution containing 1.0 g (3.4 mmole) of 2-(4-mercaptophenyl)-3-(4-pyridyl)-6,7-dihydro-[5H]-pyrrolo[1,2-a]imidazole prepared as in Example 16 and 0.5 ml (3.6 mmole) of triethylamine in 10 ml of diglyme is added 0.48 ml (3.5mmole) of phenyl chlorothionoformate. The reaction is allowed to warm to room temperature and heated at 40° to 120° C. for several hours. Workup and chromatography in a manner analogous to that outlined in Example 18 affords the desired titled compound.

EXAMPLE 28

2[4-(2-Oxobutyl)thiophenyl]-3-(4-pyridyl)-6,7-dihydro-[5H]-pyrrolo[1,2-a]imidazole To an ice bath cooled solution containing 1.0 g (3.4 mmole) of 2-(4-mercaptophenyl)-3-(4-pyridyl)-6,7-dihydro-[5H]-pyrrolo[1,2-a]imidazole prepared as in Example 16 and 0.5 ml (3.6 mmole) of triethylamine in 10 ml of methylene chloride is added 0.36 ml (3.5 mmole) of 1-bromo-2-butanone. The reaction is allowed to warm to room temperature and stirred at room temperature for several hours. Workup and chromatography in a manner analogous to that outlined in Example 18 affords the desired titled compound.

EXAMPLE 29

2-(4-Methoxymethylthiophenyl)-3-(4-pyridyl)-6,7-dihydro-[5H]-pyrrolo[1,2-a]imidazole To an ice-bath cooled solution containing 1.0 g (3.4 mmole) of 2-(4-mercaptophenyl)-3-(4-pyridyl)-6,7-dihydro-[5H]-pyrrolo[1,2 -a]imidazole prepared as in Example 16 and 0.5 ml (3.6 mmole) of triethylamine in 10 ml of methylene chloride is added 0.27 ml (3.5 mmole) of bromomethyl methyl ether. The reaction is allowed to warm to room temperature and stirred at room temperature for several hours. Workup and chromatography in a manner analogous to that outlined in example 18 affords the desired titled compound.

EXAMPLE 30

2,2-Propan-diyl-bis[2-(4-thiophenyl)3-(4-pyridyl)-6,7-dihydro-[5H]pyrrolo[1,2-a]imidazole To an ice bath cooled solution containing 1.0 g (3.4 mmole) of 2-(4-mercaptophenyl)-3-(4-pyridyl)6,7-dihydro-[5H]-pyrrolo[1,2-a]imidazole prepared as in Example 16 and 0.12 ml (1.7 mmole) of acetone in 5 ml of methylene chloride is added 0.10 ml of boron trifluoride etherate. After 4 hours at 0° C. the reaction is diluted with methylene chloride and worked up as outlined in Example 18. Purification by chromatography on silica affords the desired dithioketal.

EXAMPLE 31

2-(4-Mercaptophenyl)-3-(4-pyridyl)-6,7-dihydro-[5H]-pyrrolo[1,2-a]imidazole disulfide 2.0 (6.8 mmole) of 2-(4-mercaptophenyl)-3-(4-pyridyl)-6,7-dihydro[5H]pyrrolo[1,2 -a]imidazole prepared as in Example 16 is dissolved in a solution containing 4 parts ethanol and 1 part concentrated aqueous ammonia and allowed to air oxidize in an open flash at 20°-40° C. for 1 to 4 days. The solvent is stripped in vacuo and the product is purified by chromatography on silica to yield the desired disulfide.

EXAMPLE 32

2-(4-Ethyldithiophenyl)-3-(4-pyridyl)-6,7-dihydro-[5H]-pyrrolo[1,2-a]imidazole.

Ethanesulfenyl chloride (0.33 g) is added dropwise to an ice bath cooled solution containing 1.0 g (3.4 mmole) of 2-(4-mercaptophenyl)-3-(4-pyridyl-)6,7-dihydro-[5H]-pyrrolo[1,2 -a]imidazole prepared as in Example 16 in tetrahydrofuran. The mixture is allowed to warm to room temperature. Workup yields the crude disulfide which is purified by chromatography on silica.

EXAMPLE 33

2-(4-N-Phenylaminocarbonylthiophenyl)-3-(4-pyridyl)-6,7-dihydro-[5H]-pyrrolo[1,2-a]imidazole Phenyl isocyanate (0.38 ml, 3.5 mmole) is added dropwise to a stirring ice bath cooled solution containing 1.0 g (3.4 mmole) of 2-(4-mercaptophenyl)-3-(4-pyridyl)-6,7-dihydro[5H]-pyrrolo[1,2-a]imidazole prepared as in Example 16 in tetrahydrofuran. The mixture is allowed to warm to room temperature. Workup yields the crude titled compound which is purified by chromatography on silica.

EXAMPLE 34

2-(4-N-Phenyldithiocarbamoylphenyl)-3-(4-pyridyl)-6,7-dihydro-[5H]-pyrrolo[1,2-a]imidazole Phenyl isothiocyanate (0.42 ml, 3.5 mmole) is added dropwise to a stirring ice bath cooled solution containing 1.0 g (3.4 mmole) of 2-(4-mercaptophenyl)-(4-pyridyl)-6,7-dihydro[5H]-pyrrolo[1,2 -a]imidazole prepared as in Example 16 in tetrahydrofuran. The mixture is allowed to warm to room temperature and stirred for several hours. Workup yields the crude titled compound which is purified by chromatography on silica.

EXAMPLE 35

2-(4-Dithiocarbamoylphenyl)-3-(4-pyridyl)-6,7-dihydro-[5H]-pyrrolo[1,2-a]imidazole Thiocarbamoyl chloride (336 mg, 3.5 mmole) is added dropwise to a stirring ice-bath cooled solution containing 1.0 g (3.4 mmole) of 2-(4-mercaptophenyl)-3-(4-pyridyl)-6,7-dihydro-[5H]-pyrrolo[1,2-a]imidazole prepared as in Example 16 in tetrahydrofuran. The mixture is allowed to warm to room temperature and stirred for several hours. Workup yields the crude titled compound which is purified by chromatography on silica.

EXAMPLE 36

2-(4-N,N-Dimethylaminocarbonylthiophenyl)-3-(4-pyridyl)-6,7-dihydro-[5H]-pyrrolo[1,2-a]imidazole N,N-Dimethylcarbamoyl chloride (375 mg, 3.5 mmole) is added dropwise to a stirring −20° C. solution containing 1.0 g (3.4 mmole) of 2-(4-mercaptophenyl)-3-(4-pyridyl)-6,7-dihydro-[5H]-pyrrolo[1,2 -a]imidazole prepared as in Example 16 in tetrahydrofuran. The mixture is allowed to warm to room temperature. Workup yields the crude thiocarbamate which is purified by chromatography on silica.

EXAMPLE 37

2-(4-Dithiobenzoylphenyl)-3-(4-pyridyl)-6,7-dihydro-[5H]-pyrrolo[1,2-a]imidazole Thiobenzoyl chloride (546 mg, 3.5 mmole) is added dropwise to a stirring ice bath cooled solution containing 1.0 g (3.4 mmole) of 2-(4-mercaptophenyl)-3-(4-pyridyl)-6,7-dihydro-[5H]-pyrrolo[1,2-a]imidazole prepared as in Example 16 in tetrahydrofuran. The mixture is allowed to warm to room temperature and stirred for several hours. Workup yields the crude titled compound which is purified by chromatography on silica.

EXAMPLE 38

2-(4-Methylsulfinylphenyl)-3-(4-pyridyl)-5,6,7,8-tetrahydroimidazo[1,2-a]pyridine a)

1-(4-Fluorophenyl)-2-(2-iminopiperidinyl)ethan-1-one

A solution of 15.3g (0.071 mole) of 25% sodium methoxide in methanol is added to a solution of 10 g (0.074 mole) of 2-iminopiperidine hydrochloride in 50 ml of dry methanol with stirring under argon in a ice bath. The solvent is removed in vacuo and the residue taken up in 50 ml of chloroform and filtered under argon. This solution is added dropwise to a stirred solution of 12.82 g (0.074 mole) of 2-chloro-1-(4-fluorophenyl)ethanone in 130 ml of chloroform at 15° C. After 6 hours at room temperature the solvent is concentrated in vacuo, a minimum amount of methylene chloride is added to dissolve the residue, and ether added to afford a heavy oil. The supernatant is discarded and the oil dried in vacuo to give the titled Formula (H) compound.

b)

2-(4-Fluorophenyl)-5,6,7,8-tetrahydroimidazo[1,2-a]pyridine

The Formula (H) compound prepared as described in a) above is dissolved in a minimum volume of hot water and is refluxed under argon for 24 hours. On cooling in an ice bath, a precipaitate is formed. The supernatant is decanted, the precipitate treated with 10% aqueous NaOH solution and extracted into methylene chloride. The organic phase is dried over anhydrous potassium carbonate and concentrated in vacuo. The residue is purified by chromatography on silica to afford the titled Formula (E) compound.

c)

3-(N-Ethyloxycarbonyl-1,4-dihydro-4-pyridyl)-2-(4-fluorophenyl)-5,6,7,8-tetrahydroimidazo[1,2-a]pyridine A stirred solution of 10 g (0.046 mole) of the Formula (E) compound prepared as described in b) above, dried in vacuo, in 20 ml of dry methylene chloride and 181.9 g (2.3 moles) of dry pyridine is treated over 2 hours with 25 g (0.23 mole) of ethylchloroformate maintaining the temperature below 25° C. Every 48 hours another 25 g of ethylchloroformate is added for a total of 125 g (1.15 moles). The solvent is removed in vacuo, poured into cold 5% NaHCO$_3$ solution and extracted into methylene chloride. The organic phase is dried over anhydrous K$_2$CO$_3$ and all volatile solvents removed in vacuo. The residue is dissolved in methylene chloride extracted repeatedly with 0.2M HCl until starting material removed, then washed with 5% NaHCO$_3$ solution. The organic phase is dried over anhydrous K$_2$CO$_3$, and concentrated in vacuo to afford the titled Formula (F) compound.

d) 2-(4-Fluorophenyl)-3-(4-pyridyl)-5,6,7,8-tetrahydroimidazo[1,2-a]pyridine 15 g (0.041 mole) of the Formula (F) compound prepared as described in c) above is added to a stirred solution of 13.8 g (0.123 mole) of potassium tert-butoxide in 125 ml of dry (sieve) tert-butanol into which $O_2$ is bubbled. The solution is heated to reflux under argon until all the starting material is consumed, and the solvent is then removed in vacuo. The product is isolated as described in Example 2, Method B above, purified by flash chromatography on silica and dried in vacuo to afford the titled Formula (I) compound.

e) 2-(4-Methylthiophenyl)-3-(4-pyridyl)-5,6,7,8-tetrahydroimidazo[1,2-a]pyridine A stirred solution of 5 g (0.017 mole) of the compound prepared in d) above in 50 ml of dry (sieve) dimethylformamide is treated with 1.47 g (0.021 mole) of sodium thiomethylate at 95° C. overnight. The titled product is isolated as described in Example 22c.

f) 2-(4-Methylsulfinylphenyl)-3-(4-pyridyl)-5,6,7,8-tetrahydroimidazo[1,2-a]pyridine A stirred solution of 2 g (6.2 mmoles) of the compound prepared in e) above dissolved in 20 ml of water containing 4.1 ml of 3N hydrochloric acid is treated with a solution of 1.5 g (6.9 mmoles) of sodium periodate dropwise at 5° C. over 1.5 hours in 20 ml of water. This reaction mixture is treated as in Example 21(c) to afford the titled compound.

EXAMPLE 39—CAPSULE COMPOSITION

A pharmaceutical composition of this invention in the form of a capsule is prepared by filling a standard two piece hard gelatin capsule with 50 mg. of a compound of Formula (I), in powdered form, 110 mg. of lactose, 32 mg. of talc and 8 mg. of magnesium stearate.

EXAMPLE 40—INJECTABLE PARENTERAL COMPOSITION

A pharmaceutical composition of this invention in a form suitable for administration by injection is prepared by stirring 1.5% by weight of a compound of Formula (I) in 10% by volume propylene glycol and water. The solution is sterilized by filtration.

EXAMPLE 41—OINTMENT COMPOSITION

Compound of Formula (I) 1.0 g
White soft paraffin to 100.0 g

The compound of Formula (I) is dispersed in a small volume of the vehicle and this dispersion is gradually incorporated into the bulk to produce a smooth, homogeneous product which is filled into collapsible metal tubes.

EXAMPLE 42—TOPICAL CREAM COMPOSITION

Compound of Formula (I) 1.0 g
Polawax GP 200 20.0 g
Lanolin Anhydrous 2.0 g
White Beeswax 2.5 g
Methyl hydroxybenzoate 0.1 g
Distilled Water to 100.0 g The polawax, beeswax and lanolin are heated together at 60° C. and added to a solution of methyl hydroxybenzoate. Homogenization is achieved using high speed stirring and the temperature is allowed to fall to 50° C. The compound of Formula (I) is added and dispersed throughout, and the composition is allowed to cool with slow speed stirring.

EXAMPLE 43—TOPICAL LOTION COMPOSITION

Compound of Formula (I) 1.0 g
Sorbitan Monolaurate 0.6 g
Polysorbate 20 0.6 g
Cetostearyl Alcohol 1.2 g
Glycerin 6.0 g
Methyl Hydroxybenzoate 0.2 g
Purified Water B.P. to 100.00 ml The methyl hydroxybenzoate and glycerin are dissolved in 70 ml of the water at 75°. The sorbitan monolaurate, polysorbate 20 and cetostearyl alcohol are melted together at 75° C. and added to the aqueous solution. The resulting emulsion is homogenized, allowed to cool with continuous stirring and the compound of Formula (I) is added as a suspension in the remaining water. The whole suspension is stirred until homogenized.

EXAMPLE 44—EYE DROP COMPOSITION

Compound of Formula (I) 0.5 g
Methyl Hydroxybenzoate 0.01 g
Propyl Hydroxybenzoate 0.04 g
Purified Water B.P. to 100.00 ml The methyl and propyl hydroxybenzoates are dissolved in 70 ml purified water at 75° C. and the resulting solution is allowed to cool. The compound of Formula (I) is then added, and the solution is made up to 100 ml with purified water. The solution is sterilized by filtration through a membrane filter (0.22 mu m pore size) and packed aseptically into suitable sterile containers.

EXAMPLE 45—COMPOSITION FOR ADMINISTRATION BY INHALATION

For an aerosol container with a capacity of 15-20 ml: Mix 10 mg of a compound of Formula (I) with 0.1–0.2% of a lubricating agent, such as Span 85 or oleic acid, and disperse such mixture in a propellant (c.a.), such as freon, preferably a combination of freon 114 and freon 12, and put into an appropriate aerosol container adapted for either intranasal or oral inhalation administration.

EXAMPLE 46—COMPOSITION FOR ADMINISTRATION BY INHALATION

For an aerosol container with a capacity of 15-20 ml: Dissolve 10 mg of a compound of Formula (I) in ethanol (6–8 ml), add 0.1–0.2% of a lubricating agent, such as Span 85 or oleic acid, and disperse such in a propellant (c.a.), such as freon, preferably a combination of freon 144 and freon 12, and put into an appropriate aerosol container adapted for either intranasal or oral inhalation administration.

What is claimed is:

1. A compound of the formula

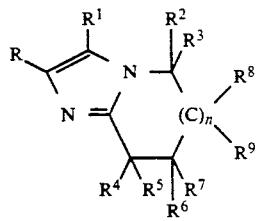

FORMULA (I)

wherein
1) One of R or $R^1$ must be alkyl substituted pyridyl and the other is selected from:
   (a) monosubstituted phenyl wherein said substituent is selected from H, halo, hydroxy $C_{1-3}$ alkoxy, $C_{1-3}$ alkylthio, $C_{1-4}$ alkyl, $C_{1-3}$ alkylsulfinyl, $C_{1-3}$ alkylsulfonyl, $C_{1-3}$ alkylamino, $C_{1-3}$ dialkylamino, $CF_3$, N-($C_{1-3}$ alkyl)-N-($C_{1-3}$alkanamido), N-pyrrolidino, N-piperidino, prop-2-ene-1-oxy or 2,2,2-trihaloethoxy;
   (b) disubstituted phenyl wherein said substituents are the same and are selected from halo, $C_{1-3}$ alkoxy, $C_{1-3}$ alkylamino, $C_{1-3}$ dialkylamino, N-pyrrolidino, N-piperidino, 2,2,2-trihaloethoxy, prop-2-ene-1-oxy, or hydroxy, or the disubstituents together form a methylene dioxy group;
   (c) disubstituted phenyl wherein said substituents are not the same and are independently selected from halo, $C_{1-3}$ alkylamino, nitro, N-($C_{1-3}$alkyl)-N-($C_{1-3}$ alkanamido, $C_{1-3}$ dialkylamino, amino, N-pyrrolidino or N-piperidino;
   (d) disubstituted phenyl wherein one of said substituents must be $C_{1-3}$ alkoxy, hydroxy, 2,2,2-trihaloethoxy or prop-2-ene-1-oxy and the other substituent is independently selected from halo, $C_{1-3}$ alkylamino, N-($C_{1-3}$alkyl)-N-$C_{1-3}$ alkanamido), $C_{1-3}$dialkylamino, amino, N-pyrrolidino or N-piperidino; or
   (e) disubstituted phenyl wherein one substituent is selected from $C_{1-3}$ alkylthio, $C_{1-3}$ alkylsulfinyl, and $C_{1-3}$ alkylsulfonyl and the other is selected from $C_{1-3}$ alkoxy. nitro, halo, amino, $C_{1-3}$ alkylamino, or $C_{1-3}$ dialkylamino; or
2) One of R or $R^1$ is 2-pyridyl or 3-pyridyl and the other is selected from:
   (a) monosubstituted phenyl wherein said substituent is selected from $C_{1-3}$ alkylthio, $C_{1-3}$ alkylsulfinyl, $C_{1-3}$ alkylsulfonyl, $C_{1-3}$alkoxy or hydroxy; or
   (b) disubstituted phenyl wherein one substituent is selected from $C_{1-3}$ alkylthio, $C_{1-3}$ alkylsulfinyl, or $C_{1-3}$ alkylsulfonyl and the other is selected from $C_{1-3}$ alkoxy, nitro, halo, amino, $C_{1-3}$ alkylamino, or $C_{1-3}$ dialkylamino; or
3) R is 4-pyridyl and $R^1$ is selected from:
   (a) monosubstituted phenyl wherein said substituent is selected from $C_{1-3}$ alkylthio, $C_{1-3}$ alkylsulfinyl, $C_{1-3}$ alkylsulfonyl or hydroxy; or
   (b) disubstituted phenyl wherein one substituent is selected from $C_{1-3}$ alkylthio, $C_{1-3}$ alkylsulfinyl, or $C_{1-3}$ alkylsulfonyl and the other is selected from $C_{2-3}$ alkoxy, nitro, halo, amino, $C_{1-3}$ alkylamino, or $C_{1-3}$ dialkylamino; or
4) $R^1$ is 4-pyridyl and R selected from:
   (a) monosubstituted phenyl wherein said substituent is selected from $C_{1-3}$ alkylthio, $C_{1-3}$ alkylsulfinyl, $C_{1-3}$ alkylsulfonyl, hydroxy, $C_{2-3}$ alkoxy, or a branched or unbranched $C_{2-5}$alkenylthio or $C_{2-5}$alkenylsulfinyl; or
   (b) disubstituted phenyl wherein one substituent is selected from $C_{1-3}$ alkylthio, $C_{1-3}$ alkylsulfinyl, or $C_{1-3}$ alkylsulfonyl and the other is selected from $C_{2-3}$ alkoxy, nitro, halo, amino, $C_{1-3}$ alkylamino, $C_{1-3}$ dialkylamino, or a branched or unbranched $C_{2-5}$ alkenylthio or $C_{2-5}$ alkenylsulfinyl; or $R^2$, $R^3$, $R^4$, $R^5$, $R^6$, $R^7$, $R^8$ and $R^9$ are H, or one or two of $R^2$, $R^3$, $R^3$, $R^4$, $R^5$, $R^6$, $R^7$, $R^8$ and $R^9$ are independently selected from H or $C_{1-2}$ alkyl; n is 0 or 1;

or a pharmaceutically acceptable salt thereof.

2. The compound of claim 1 which is 2-(4-methylthiophenyl)-3-(4-pyridyl-)-6,7-dihydro-[5H]-pyrollo[1,2-a]imidazole.

3. The compound of claim 1 which is 2-(4-methylsulfinylphenyl)-3-(4-pyridyl)-6,7-dihydro-[5H]-pyrrolo[1,2-a]imidazole.

4. The compound of claim 1 which is:
2-(4-methylsulfonylphenyl)-3-(4-pyridyl)-6,7-dihydro-[5H]-pyrrolo[1,2-a]imidazole,
2-(4-methoxyphenyl)-3-(2-pyridyl)-6,7-dihydro-[5H]-pyrrolo[1,2-a]imidazole,
2-(4-methoxyphenyl)-3-(3-pyridyl)-6,7-dihydro-[5H]-pyrrolo[1,2-a]imidazole,
2-(4-methoxyphenyl)-3-(2,6-dimethyl-4-pyridyl)-6,7-dihydro-[5H]-pyrrolo[1,2-a]imidazole
2-(4-hydroxyphenyl)-(3-(4-pyridyl)-6,7-dihydro-[5H]-pyrrolo-[1,2-a]imidazole dihydrobromide,
2-(4-ethoxyphenyl)-3-(4-pyridyl)-6,7-dihydro-[5H]-pyrrolo-[1,2-a]imidazole,
2-[4-(1-propoxy)phenyl]-3-(4-pyridyl)-6,7-dihydro-[5H]-pyrrolo[1,2-a]imidazole,
2-[4-(2-propoxy)phenyl]-3-(4-pyridyl)-6,7-dihydro-[5H]-pyrrolo[1,2-a]imidazole,
2-(4-ethylsulfinylphenyl)-3-(4-pyridyl)-6,7-dihydro-[5H]-pyrrolo[1,2-a]imidazole,
2-(4-ethylthiophenyl)-3-(4-pyridyl)-6,7-dihydro-[5H]-pyrrolo[1,2-a]imidazole,
2-(4-mercaptophenyl) 3-(4-pyridyl)-6,7-dihydro-[5H]-pyrrolo[1,2-a]imidazole,
2-(4-ethylsulfonylphenyl)-3-(4-pyridyl)-6,7-dihydro-[5H]-pyrrolo[1,2-a]imidazole,
3-(4-methylsulfinylphenyl)-2-(4-pyridyl)-6,7-dihydro-[5H]-pyrrolo[1,2-a]imidazole,
2-(4-methylsulfinylphenyl)-3-[4(2-methyl)pyridyl]-6,7-dihydro-[5H]-pyrrolo[1,2-a]imidazole,
2-(4-carbethoxymethylthiophenyl)-3-(4-pyridyl)-6,7-dihydro-[5H]-pyrrolo[1,2-a]imidazole,
2-(4-acetoxymethylthiophenyl)-3-(4-pyridyl)-6,7-dihydro-[5H]-pyrrolo[1,2-a]imidazole,
2-[4-fluorophenyl)-3-[4-(2-methyl)pyridyl]-6,7-dihydro-[5H]-pyrrolo[1,2-a]imidazole, or
2-(4-methoxyphenyl)-3-[4-(2-methyl)pyridyl]-6,7-dihydro-[5H]-pyrrolo[1,2-a]imidazole.

5. A pharmaceutical composition comprising a pharmaceutically acceptable carrier or diluent and an effective 5-lipoxygenase pathway inhibiting amount of a compound of claim 1.

6. The composition of claim 5 wherein the composition is in dosage unit form adapted for parenteral administration.

7. The composition of claim 6 which comprises from about 50 mg to about 500 mg of the active compound.

8. The composition of claim 5 wherein the composition is in dosage unit form adapted for oral administration.

9. The composition of claim 8 which comprises from about 100 mg to about 1000 mg of the active compound.

10. The composition of claim 5 wherein the composition is in a dosage unit form adapted for administration by inhalation.

11. The composition of claim 5 wherein the composition is in a dosage unit form adapted for topical administration.

12. The composition of claim 5 wherein the active ingredient is 2-(4-methylthiophenyl)-3-(4-pyridyl)-6,7-dihydro-[5H]-pyrrolo[1,2-a]imidazole, 2-(4-methylsulfinylphenyl)-3-(4-pyridyl)-6,7-dihydro-[5H]-pyrrolo[1,2-a]imidazole, 2-(4-methylsulfonylphenyl)-3-(4-pyridyl)-6,7-dihydro-[5H]-pyrrolo[1,2-a]imidazole, 2-(4-methoxyphenyl)-3-(2-pyridyl)-6,7-dihydro-[5H]-pyrrolo[1,2-a]imidazole, 2-(4-methoxyphenyl)-3-(3-pyridyl)-6,7-dihydro-[5H]-pyrrolo[1,2-a]imidazole, 2-(4-methoxyphenyl)-3-(2,6-dimethyl-4-pyridyl)-6,7-dihydro-[5H]-pyrrolo[1,2-a]imidazole, 2-(4-hydroxyphenyl)-3-(4-pyridyl)-6,7-dihydro-[5H]-pyrrolo[1,2-a]imidazole dihydrobromide;

2-(4-ethoxyphenyl)-3-(4-pyridyl)-6,7-dihydro-[5H]-pyrrolo[1,2-a]imidazole,

2-[4-(1-propoxy)phenyl]-3-(4-pyridyl)-6,7-dihydro-[5H]-pyrrolo[1,2-a]imidazole,

2-[4-(2-propoxy)phenyl]-3-(4-pyridyl)-6,7-dihydro-[5H]-pyrrolo[1,2-a]imidazole, 2-(4-ethylthiophenyl)-3-(4-pyridyl)-6,7-dihydro-[5H]-pyrrolo[1,2-a]imidazole, 2-(4-ethylsulfinylphenyl)-3-(4-pyridyl)-6,7-dihydro-[5H]-pyrrolo[1,2-a]imidazole, 2-(4-mercaptophenyl)-3-(4-pyridyl)-6,7-dihydro-[5H]-pyrrolo[1,2-a]imidazole, 2-(4-trimethylacetylthiophenyl)-3-(4-pyridyl)-6,7-dihydro-[5H]-pyrrolo[1,2-a]imidazole, 2-(4-acetylthiophenyl)-3-(4-pyridyl)6,7-dihydro-[5H]-pyrrolo(1,2-a]imidazole, 2-(4-ethylsulfonylphenyl)-3-(4-pyridyl)-6,7-dihydro-[5H]-pyrrolo[1,2-a]imidazole, 3-(4-methylsulfinylphenyl)-2-(4-pyridyl)6,7-dihydro-[5H]-pyrrolo[1,2-a]imidazole, 2-(4-methylsulfinylphenyl)-3-[4-(2-methyl)pyridyl]-6,7-dihydro-[5H]-pyrrolo[1,2-a]imidazole, 2-(4-carbethoxymethylthiophenyl)-3-(4-pyridyl)-6,7-dihydro-[5H]-pyrrolo[1,2-a]imidazole, 2-(4-acetoxymethylthiophenyl)-3-(4-pyridyl)-6,7-dihydro-[5H]-pyrrolo[1,2-a]imidazole, 2-(4-methylthiophenyl)-3-[4-(2-methyl)pyridyl]-6,7-dihydro-[5H]-pyrrolo[1,2-a]imidazole, 3-(4-methylthiophenyl)-2-[4-pyridyl]-6,7-dihydro-[5H]-pyrrolo[1,2-a]imidazole, 2-[4-fluorophenyl]-3-[4-(2-methyl)pyridyl]-6,7-dihydro-[5H]-pyrrolo[1,2-a]imidazole, or 2-(4-methoxyphenyl)-3-[4-(2-methyl)pyridyl]-6,7-dihydro-[5H]-pyrrolo[1,2-a]imidazole.

13. A method of treating a 5-lipoxygenase pathway mediated disease in a subject in need thereof which comprises administering to such subject an effective, non-toxic 5-lipoxygenase pathway inhibiting amount of a compound of claim 1.

14. A method of treating osteoarthritis in a subject in need thereof which comprises administering to such subject an effective, non-toxic 5-lipoxygenase pathway inhibiting amount of a compound of claim 1.

15. A compound of the formula

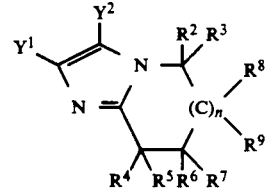

FORMULA (L)

wherein:

n is 0 or 1, $R^2$, $R^3$, $R^4$, $R^5$, $R^6$, $R^7$, $R^8$, $R^9$ are all H, or one or two of $R^2$, $R^3$, $R^4$, $R^5$, $R^6$, $R^7$, $R^8$ and $R^9$, are independently selected from H or $C_{1-2}$ alkyl;

one of $Y^1$ or $Y^2$ is independently selected from 4-[1,2-dihydro-2-($C_{1-4}$-alkyl)pyridyl substituted with N-($C_{1-8}$ alkanoyl), N-($C_{1-8}$ alkoxycarbonyl), N-(benzoyl), N-(phenoxycarbonyl), N-(phenylacetyl), or N-(benzyloxycarbonyl);

and the other is selected from (a) monosubstituted phenyl wherein said substituent is selected from H, halo, $C_{1-3}$ alkoxy, $C_{1-3}$ alkylthio, $C_{1-4}$ alkyl, N-($C_{1-3}$ alkyl)-N-($C_{1-3}$ alkanamido), $C_{1-3}$ dialkylamino, $CF_3$, N-pyrrolidino, N-piperidino, prop-2-ene-1-oxy or 2,2,2-trihaloethoxy;

(b) disubstituted phenyl wherein said substituents are the same and are selected from halo, $C_{1-3}$ alkoxy, $C_{1-3}$ dialkylamino, $C_{1-3}$alkylthio, N-pyrrolidino, N-piperidino, 2,2,2-trihaloethoxy, or prop-2-ene-1-oxy, or the disubstituents together form a methylene dioxy group;

(c) disubstituted phenyl wherein said substituents are not the same and are independently selected from halo, N-($C_{1-3}$ alkyl)-N-($C_{1-3}$ alkanamido), $C_{1-3}$ dialkylamino, N-pyrrolidino, or N-piperidino; or (d) disubstituted phenyl wherein one of said substituents must be $C_{1-3}$ alkoxy, $C_{1-3}$ alkylthio, 2,2,2-trihaloethoxy or prop-2-ene-1-oxy and the other substituent is independently selected from halo, $C_{1-3}$ alkylamino, N-($C_{1-3}$ alkyl)-N-($C_{1-3}$ alkanamido), $C_{1-3}$dialkylamino, N-pyrrolidino, or N-piperidino;

or a salt thereof.

* * * * *